US008658373B2

(12) United States Patent
Nakao et al.

(10) Patent No.: US 8,658,373 B2
(45) Date of Patent: Feb. 25, 2014

(54) METHOD OF SCREENING FOR AN AGENT FOR TREATING ARTHRITIS AND PROMOTING GROWTH OF ARTICULAR CHONDROCYTES

(75) Inventors: Kazuwa Nakao, Kyoto (JP); Hidetomo Kitamura, Gotenba (JP)

(73) Assignees: Kazuwa Nakao, Kyoto-Shi (JP); Chugai Seiyaku Kabushiki Kaisha, Tokyo (JP)

(*) Notice: Subject to any disclaimer, the term of this patent is extended or adjusted under 35 U.S.C. 154(b) by 110 days.

(21) Appl. No.: 12/623,936

(22) Filed: Nov. 23, 2009

(65) Prior Publication Data

US 2010/0209958 A1  Aug. 19, 2010

Related U.S. Application Data

(62) Division of application No. 10/594,920, filed as application No. PCT/JP2005/006831 on Mar. 31, 2005, now Pat. No. 7,642,243.

(30) Foreign Application Priority Data

Mar. 31, 2004  (JP) ................................. 2004-107924

(51) Int. Cl.
*G01N 33/53* (2006.01)
*C07K 14/705* (2006.01)

(52) U.S. Cl.
USPC .......................................... 435/7.1; 530/350

(58) Field of Classification Search
None
See application file for complete search history.

(56) References Cited

U.S. PATENT DOCUMENTS

| | | | |
|---|---|---|---|
| 4,446,129 A | 5/1984 | Sawada et al. | |
| 5,340,920 A | 8/1994 | Matsuo et al. | |
| 5,434,133 A | 7/1995 | Tanaka et al. | |
| 5,443,133 A | 8/1995 | Dreilich et al. | |
| 6,034,231 A | 3/2000 | Tanaka et al. | |
| 6,743,425 B2 | 6/2004 | Nakao et al. | |
| 2003/0068313 A1 | 4/2003 | Nakao | |
| 2004/0138285 A1 | 7/2004 | Okazaki | |
| 2004/0198665 A1 | 10/2004 | Nakao | |

FOREIGN PATENT DOCUMENTS

| | | |
|---|---|---|
| CN | 2005-80017490.5 | 1/2007 |
| CN | 200580017490.5 | 5/2009 |
| EP | 0863134 A1 | 9/1998 |
| JP | 59-51221 A | 3/1984 |
| JP | 4-74198 A | 3/1992 |
| JP | 4-327598 A | 11/1992 |
| JP | 10-251220 A | 9/1998 |
| JP | 10-509146 A | 9/1998 |
| JP | 11-196873 A | 7/1999 |
| JP | 2002-356437 A | 12/2002 |
| JP | 2003-104908 | 4/2003 |
| JP | 2003-113116 A | 4/2003 |
| WO | 96/15096 A1 | 5/1996 |
| WO | WO-02/074234 | 9/2002 |
| WO | WO-02/087620 A1 | 11/2002 |

OTHER PUBLICATIONS

Koller et al (1991. Science. 252: 120-123).*
Khatib et al, 1998. Cytokine. 10(9): 669-679.*
Yasato Komatsu et al., Clinical Calcium, 2003, 13(12), pp. 1578 to 1581.
Yasoda, A et al., J. Biol. Chem., 1998, 273(19), pp. 11695 to 11700.
Yasato Komatsu, Heisei 15 Nendo Sokatsu Buntan Kenkyu Hokokusho (Kosei Rodo Kagaku Kenkyuhi Hojokin Human Genome Saisei Iryo Nado Kenkyu Jigyo), Mar. 2004, pp. 10 to 13.
Hiroshi Kawaguchi, Journal of Clinical Medicine, 2005, 63 (Zokango 1), pp. 676 to 679.
Johnson et al., J. of Biological Chemistry, vol. 278, No. 21, pp. 18824-18832, (2003).
Kiemer et al., Endocrinology, vol. 143, No. 3, pp. 846-852, (2002).
Yasoda et al., Nature Medicine, vol. 10, No. 1, pp. 80-86, (2004).
Aigner et al., Apoptosis and Cellular Vitality; Issues in Osteoarthritic Cartilage Degeneration, Arthritis & Rheumatism, vol. 4, No. 8, Aug. 2002, pp. 1986-1996.
Abbey et al., "Lysophosphatidic Acid Inhibits C-Type Natriuretic Peptide Activation of Guanylyl Cyclase-B," *Endocrinology*, vol. 144, No. 1, Jan. 2003, pp. 240-246.
Komatsu et al., "CNP/Guanylyl Cyclase B (GC-B) System Regulates Endochondral Ossification—The Analysis of GC-B Null Mice," *Journal of Bone and Mineral Research*, vol. 20, No. 9, Suppl. 1, Sep. 2005, p. S61.
Ozasa et al., "Complementary Antagonistic Actions Between C-type Natriuretic Peptide and the MAPK Pathway Through FGFR-3 in ATDC5 Cells," Bone, vol. 36, No. 6, Jun. 2005, pp. 1056-1064.
Schulz, 2005, Peptides, vol. 26, pp. 1024-1034.
Mahomed et al., 1998, American Journal of Medical Genetics, vol. 78, pp. 30-35.
The Supplementary European Search Report for European Patent Appl. No. 05728888.8, dated Aug. 13, 2009.
Japanese Office Action dated Feb. 15, 2011 for Japanese Application No. 2006-511895.
Australian Office Action dated May 19, 2011 for Application No. 2005228817.
Japanese Office Action dated May 24, 2011 for Application No. 2006-511895.
Koichi et al., "Special Topic II, New Cytokines and Chemokines, Cytokines involved in osteogenesis", Inflammation & Immunity, vol. 11, No. 4, pp. 459-465, (2003).
Suzuki et al., "Influence of Nonsteroidal Anti-inflammatory Drugs on the Proliferation of Cultured Rabbit-Chondrocytes", J. New Remedies & Clinics, vol. 45, No. 5, May 1996, pp. 1004-1008.
Wu et al., "Furin-mediated Processing of Pro-C-type Natriuretic Peptide", The Journal of Biological Chemistry, vol. 278, No. 28, Jul. 11, 2003, pp. 25847-25852.

* cited by examiner

*Primary Examiner* — Zachary Howard

(74) *Attorney, Agent, or Firm* — Birch, Stewart, Kolasch & Birch, LLP

(57) ABSTRACT

This invention provides a new therapeutic or prophylactic agent for arthritis such as osteoarthritis. Specifically, it provides a therapeutic or prophylactic agent for arthritis such as osteoarthritis, or an agent for promoting the growth of articular chondrocyte, comprising a guanyl cyclase B (GC-B) activator as an active ingredient; or a method for inhibiting arthritis or for promoting the growth of articular chondrocyte by activating GC-B; or a method for screening an agent for promoting the growth of articular chondrocyte or an agent capable of treating arthritis using the GC-B activity as an indication.

14 Claims, 13 Drawing Sheets

(3 of 13 Drawing Sheet(s) Filed in Color)

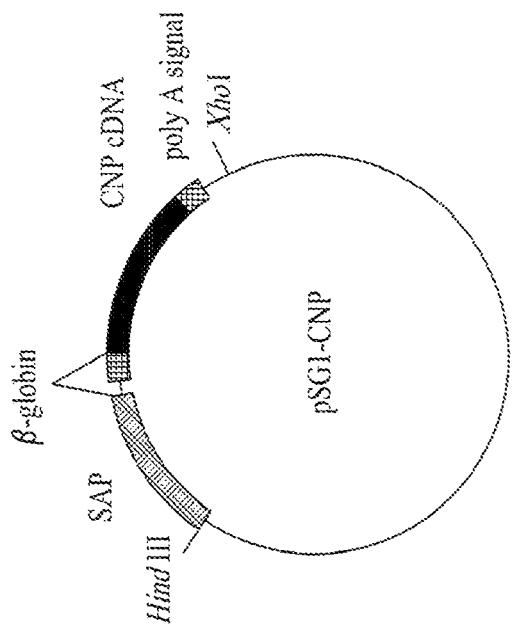
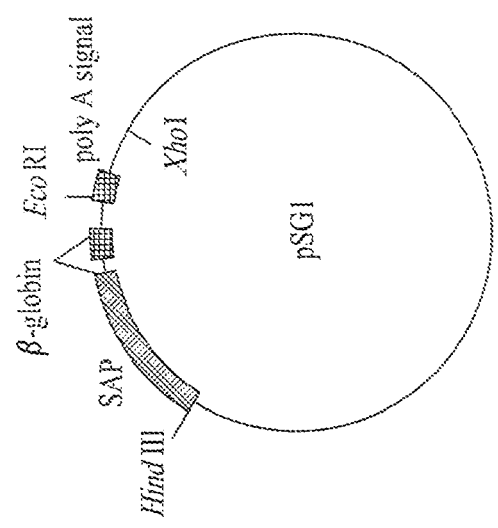
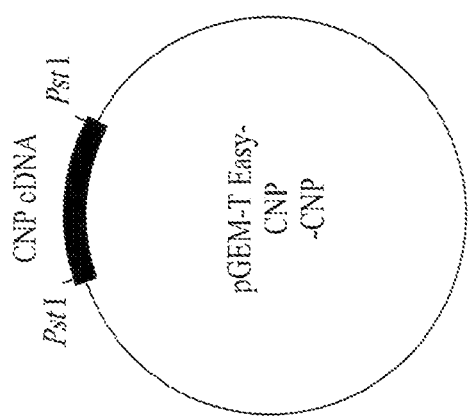

Normal synovial tissue

3% collagenase, wild type

3% collagenase,
CNP transgenic mouse tgm strain #17

Normal articular cartilage

3% collagenase, wild type

3% collagenase,
CNP transgenic mouse tgm strain #17

```
                        SEQUENCE LISTING

<160> NUMBER OF SEQ ID NOS: 10

<210> SEQ ID NO 1
<211> LENGTH: 22
<212> TYPE: PRT
<213> ORGANISM: Homo sapiens
<220> FEATURE:
<221> NAME/KEY: DISULFID
<222> LOCATION: (6)..(22)
<223> OTHER INFORMATION: A disulfide bond is formed

<400> SEQUENCE: 1

Gly Leu Ser Lys Gly Cys Phe Gly Leu Lys Leu Asp Arg Ile Gly Ser
 1               5                  10                  15

Met Ser Gly Leu Gly Cys
            20

<210> SEQ ID NO 2
<211> LENGTH: 53
<212> TYPE: PRT
<213> ORGANISM: Homo sapiens
<220> FEATURE:
<221> NAME/KEY: DISULFID
<222> LOCATION: (37)..(53)
<223> OTHER INFORMATION: A disulfide bond is formed

<400> SEQUENCE: 2

Asp Leu Arg Val Asp Thr Lys Ser Arg Ala Ala Trp Ala Arg Leu Leu
 1               5                  10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 3
<211> LENGTH: 22
```

```
<212> TYPE: PRT
<213> ORGANISM: Artificial Sequence
<220> FEATURE:
<223> OTHER INFORMATION: Description of Artificial Sequence:  Synthetic
      CNP-22 derivative derived from mammals
<220> FEATURE:
<221> NAME/KEY: DISULFID
<222> LOCATION: (6)..(22)
<223> OTHER INFORMATION: A disulfide bond is formed

<400> SEQUENCE: 3

Gly Leu Ser Lys Gly Cys Phe Gly Leu Lys Leu Asp Arg Ile Gly Ala
 1               5                  10                  15

Met Ser Gly Leu Gly Cys
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence:  Synthetic
      CNP-22 derivative derived from mammals
<220> FEATURE:
<221> NAME/KEY: DISULFID
<222> LOCATION: (6)..(22)
<223> OTHER INFORMATION: A disulfide bond is formed

<400> SEQUENCE: 4

Gly Leu Ser Lys Gly Cys Phe Gly Leu Lys Leu Asp Arg Ile Gly Ser
 1               5                  10                  15

Gln Ser Gly Leu Gly Cys
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence:  Synthetic
      CNP-22 derivative derived from mammals
<220> FEATURE:
<221> NAME/KEY: DISULFID
<222> LOCATION: (6)..(22)
<223> OTHER INFORMATION: A disulfide bond is formed

<400> SEQUENCE: 5

Gly Leu Ser Lys Gly Cys Phe Gly Leu Lys Leu Asp Arg Ile Gly Ser
 1               5                  10                  15

Ala Ser Gly Leu Gly Cys
            20

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence:  Synthetic
      CNP-22 derivative derived from mammals
<220> FEATURE:
<221> NAME/KEY: DISULFID
<222> LOCATION: (1)..(17)
<223> OTHER INFORMATION: A disulfide bond is formed

<400> SEQUENCE: 6

Cys Phe Gly Leu Lys Leu Asp Arg Ile Gly Ser Met Ser Gly Leu Gly
 1               5                  10                  15

Cys
```

```
<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      CNP-22 derivative derived from mammals
<220> FEATURE:
<221> NAME/KEY: DISULFID
<222> LOCATION: (7)..(23)
<223> OTHER INFORMATION: A disulfide bond is formed

<400> SEQUENCE: 7

Ser Leu Arg Arg Ser Ser Cys Phe Gly Leu Lys Leu Asp Arg Ile Gly
 1               5                  10                  15

Ser Met Ser Gly Leu Gly Cys
            20

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      CNP-22 derivative derived from mammals
<220> FEATURE:
<221> NAME/KEY: DISULFID
<222> LOCATION: (6)..(22)
<223> OTHER INFORMATION: A disulfide bond is formed

<400> SEQUENCE: 8

Gly Leu Ser Lys Gly Cys Phe Gly Leu Lys Leu Asp Arg Ile Gly Ser
 1               5                  10                  15

Met Ser Gly Leu Gly Cys Asn Ser Phe Arg Tyr
            20                  25

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      CNP-22 derivative derived from mammals
<220> FEATURE:
<221> NAME/KEY: DISULFID
<222> LOCATION: (1)..(17)
<223> OTHER INFORMATION: A disulfide bond is formed

<400> SEQUENCE: 9

Cys Phe Gly Leu Lys Leu Asp Arg Ile Gly Ser Gln Ser Gly Leu Gly
 1               5                  10                  15

Cys Asn Ser Phe Arg Tyr
            20

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      CNP-22 derivative derived from mammals
<220> FEATURE:
<221> NAME/KEY: MUTAGEN
<222> LOCATION: (4)..(4)
<223> OTHER INFORMATION: Xaa is Leu, Ile, or Val
<220> FEATURE:
<221> NAME/KEY: MUTAGEN
<222> LOCATION: (5)..(5)
<223> OTHER INFORMATION: Xaa is Lys, Leu, or Met
<220> FEATURE:
```

```
-continued

<221> NAME/KEY: MUTAGEN
<222> LOCATION: (6)..(6)
<223> OTHER INFORMATION: Xaa is Leu, Ile, Ala, or Val
<220> FEATURE:
<221> NAME/KEY: MUTAGEN
<222> LOCATION: (11)..(11)
<223> OTHER INFORMATION: Xaa is Ser, Ala, Gly, Thr, or Asn
<220> FEATURE:
<221> NAME/KEY: MUTAGEN
<222> LOCATION: (12)..(12)
<223> OTHER INFORMATION: Xaa is Met, Ala, Trp, His, Lys, Ser, or Gly
<220> FEATURE:
<221> NAME/KEY: MUTAGEN
<222> LOCATION: (12)..(12)
<223> OTHER INFORMATION: Xaa is Met, Ala, Trp, His, Lys, Ser, or Gly
<220> FEATURE:
<221> NAME/KEY: MUTAGEN
<222> LOCATION: (14)..(14)
<223> OTHER INFORMATION: Xaa is Gly, Lys, Ala, or Leu
<220> FEATURE:
<221> NAME/KEY: MUTAGEN
<222> LOCATION: (15)..(15)
<223> OTHER INFORMATION: Xaa is Leu or Met
<220> FEATURE:
<221> NAME/KEY: DISULFID
<222> LOCATION: (1)..(17)
<223> OTHER INFORMATION: A disulfide bond is formed

<400> SEQUENCE: 10

Cys Phe Gly Xaa Xaa Xaa Asp Arg Ile Gly Xaa Xaa Ser Xaa Xaa Gly
 1               5                   10                  15

Cys
```

METHOD OF SCREENING FOR AN AGENT FOR TREATING ARTHRITIS AND PROMOTING GROWTH OF ARTICULAR CHONDROCYTES

This application is a Divisional of U.S. patent application Ser. No. 10/594,920, filed Sep. 29, 2006, which issued as U.S. Pat. No. 7,642,243 on Jan. 5, 2010, which is the national phase of PCT International Application No. PCT/JP05/06831 filed on Mar. 31, 2005 under 35 U.S.C. §371. This application also claims priority under 35 U.S.C. §119(a) of Patent Application No. 2004/107924 filed in Japan on Mar. 31, 2004. The entire contents of each of the above-identified applications are hereby incorporated by reference.

TECHNICAL FIELD

The present invention relates to a therapeutic or prophylactic agent for arthritis, particularly osteoarthritis and similar types of arthritic diseases, or an agent for promoting the growth of articular chondrocytes, or a method for inhibiting the arthritis or a method for promoting the growth of articular chondrocyte, using a guanyl cyclase B (hereinafter referred to as "GC-B") activator. The present invention further relates to a method for screening of a therapeutic agent for arthritis or an articular chondrocyte growth promoter using GC-B activity as an indication.

BACKGROUND ART

Arthritis is an inflammatory disease of the joint, and rheumatoid arthritis and osteoarthritis (or osteoarthrosis) are prevalent arthritic disorders.

Rheumatoid arthritis is thought to be an autoimmune disease, accompanied by articular pain, stiffening and swelling, and as the disease progresses, may often lead to the degeneration of the articular cartilage surfaces similar to osteoarthritis, resulting in severe destruction of the articular bone and cartilage.

Osteoarthritis is a degenerative disease of the articular cartilage occurring frequently in the elderly. Osteoarthritis (OA) involves destruction of the cartilage and proliferative change in the bone and cartilage resulting from degeneration of articular components, with the change resulting in a secondary arthritis (e.g., synovitis). Osteoarthritis occurs mainly in weight-bearing joints, such as the knees, elbows and hip joints (Virchows Arch 1996; 260:521-663), and less frequently in non-weight-bearing joints, such as the shoulder/elbow and hand joints. Furthermore, temporomandibular arthrosis with similar conditions has been identified in the temporomandibular joint (J Orofac Pain 1999; 13(4): 295-306).

It is known that the matrix proteins, which are the functional entity of the cartilage, are reduced, and the number of chondrocytes decreases in osteoarthritis (Arth Rheum 2002; 46(8): 1986-1996). However, due to the lack of blood vessels distributed in the cartilage tissue, the small number of chondrocytes that are highly differentiated, the small number of cartilage precursor cells, and the slow turnover of the cartilage matrix, the cartilage has too low self-reproduction ability to ensure spontaneous recovery from the decreases in articular cartilage matrix and chondrocytes in osteoarthritis (Novartis Found. Symp. 2003; 249:2-16). In addition, in osteoarthritis, arthritis occurs concurrently with the degeneration of cartilage, leading to joint pain (J Rheumatol 2001; 28(6): 1330-1337).

Examples of reported therapeutic/prophylactic agents for arthritis, such as rheumatoid arthritis and osteoarthritis, include, for example, a protein tyrosine kinase inhibitor (Japanese Patent Publication (Kohyo) No. 11-512708A (1999)), N-acyl-2-glucosamine derivatives (Japanese Patent Publication (Kohyo) No. 2004-507490A), and quinoline/quinazoline derivatives (Japanese Patent Publication (Kokai) No. 9-169646A (1997)). In addition, current standard therapeutic agents for osteoarthritis that have been used widely are oral anti-inflammatory analgesics or hyaluronic acid and adrenocortical steroid preparations for intra-articular injection, which all relieve joint pain, and this means that drugs having inhibitory effect on the degeneration of the articular cartilage are required (Decision Base 7, 2002).

Guanyl cyclase (GC) is a membrane protein belonging to the enzyme family that catalyzes the synthesis of the second messenger cGMP from GTP, and examples include GC-A, GC-B, GC-C, GC-D, GC-E, and GC-F. GC-B is found mainly in vascular endothelial cells, and thought to be involved in relaxation of the smooth muscle. A natriuretic peptide (NP) is known to activate GC. NPs are divided into ANP (atrial sodium peptide), BNP (brain natriuretic peptide) and CNP (C-type natriuretic peptide), and they are thought to exhibit biological activity by elevating intracellular cGMP level through two guanyl cyclase conjugated receptors (NPR-A for ANP and BNP, and NPR-B for CNP) (Ann Rev Biochem 1991; 60: 229-255).

NPR-C is not a guanyl cyclase conjugated receptor and thought to be a clearance receptor for NPs not involved in signal transduction (Science, 1987; 238:675-678). However, in a system by which prostaglandin $E_2$ ($PGE_2$) production is induced by cyclooxygenase 2 (COX-2) when mouse bone marrow macrophages are stimulated with lipopolysaccharide (LPS), ANP and CNP have been reported to exhibit an inhibitory effect on $PGE_2$ production by decreasing intracellular cAMP levels via NPR-C, and this suggests the involvement of NPR-C in the signal transduction of NPs (Endocrinology 2002; 143(3): 846-852). The report describes that ANP exhibits an inhibitory effect of up to about 70% on the enhancement of $PGE_2$ production through stimulation of mouse bone marrow macrophages (BMM) with LPS, while CNP exhibits only an inhibitory effect of up to about 20%, thus CNP has a weaker effect. Because the control of COX-2 production through cyclic nucleotides, such as cAMP and cGMP, is known to represent either promotional or inhibitory reaction depending on the cell type and stimulation type, it is unclear whether the inhibition of LPS-induced $PGE_2$ production in BMM cells by CNP may be applied to other cells and stimulations. In addition, Endocrinology 2002; 143(3): 846-852 reported that ANP was shown to exhibit an inhibitory effect in a system where LPS administration increased blood thromboxane $B_2$ ($TXB_2$) level in mice, and contrarily cANF of the same mechanism enhanced. In addition, although the report describes the application of ANP to immunity-related diseases, such as arthritis and sepsis, it makes no reference to the application of CNP to those related diseases. Consequently, no finding has been obtained regarding the action of CNP on arthritis.

NPs have been reported to play an important role in the control of humoral homeostasis and blood pressure (J Clin Invest 1987; 93:1911-1921, J Clin Invest 1994; 87: 1402-1412), and their expression and biological activity in various tissues other than the cardiovascular system are known (Endocrinol 1991; 129:1104-1106, Ann Rev Biochem 1991; 60: 553-575). For cartilage, the use of CNP for the extension of auxotonic gristle and treatment of achondrogenesis in transgenic mice overexpressing BNP (Proc. Natl. Acad. Sci.

U.S.A. 1998; 95:2337-2342) or CNP has been reported (Nat Med 2004; 10(1): 80-86, Japanese Patent Publication (Kokai) No. 2003-113116A). However, the growth plate cartilage is temporary cartilage that disappears eventually following calcification and displacement by bones, and it is known to have biological properties that are different from permanent cartilage which exists during lifetime, such as articular cartilage and tracheal cartilage (Dev Biol 1989; 136(2): 500-507, J Cell Biol 2001; 153(1): 87-100). Furthermore, although the in vitro activity of CNP to enhance the hypertrophy of articular chondrocytes, which is permanent cartilage, has been reported (J Biol Chem 2003; 278(21): 18824-18832), no finding has been obtained regarding the in vivo action on the articular cartilage in normal animals, or on the degeneration of the articular cartilage or arthritis in osteoarthritis.

In osteoarthritis, the articular cartilage swells at the earliest stage of the disease, resulting in a temporary increase in the cartilage tissue volume (J Rheum 1991; 18(3): 1905-1915), and with the progress of the disease, degeneration/destruction of the cartilage matrix increases, leading to a decrease in the volume (Arthritis Rheum 2004; 50(2): 476-487). The number of articular chondrocytes decreases due to apoptosis (Arthritis Rheum 2004; 50(2): 507-515). On the other hand, the remaining individual articular chondrocytes are known to express type X collagen, and differentiate into hypertrophic chondrocytes having the nature of temporary cartilage (Arthritis Rheum 1992; 35(7): 806-811). In addition, arthritis accompanies the destruction of the articular cartilage and may be a factor in clinical pain in the affected joint (J. Rheumatol. 2001; 28(6): 1330-1337). Inhibition of these changes in osteoarthritis, i.e. the decreases in or recovery of the articular cartilage matrix and the number of articular chondrocytes, and the inhibition of arthritis, is thought to be useful in the development of therapeutic agents.

It is an object of the present invention to provide a new therapeutic or prophylactic agent for arthritis, including osteoarthritis, or a method for treating the arthritis.

It is another object of the present invention to provide an agent or method for promoting the growth of articular chondrocytes.

It is another object of the present invention to provide a method for inhibiting arthritis including osteoarthritis.

It is another object of the present invention to provide a method for screening of a therapeutic agent for arthritis.

It is another object of the present invention to provide a method for screening of an agent for promoting the growth of articular chondrocyte.

SUMMARY OF THE INVENTION

We prepared a CNP transgenic mouse that overexpresses C-type natriuretic peptide (CNP), which is a kind of guanyl cyclase B (GC-B) activator, to study the effect on the articular cartilage, and the following results were obtained: in the CNP transgenic mouse, the thickness of the articular cartilage and the number of articular chondrocytes increased significantly; in an osteoarthritic model prepared from the CNP transgenic mouse, it was resistant to articular swelling, with the degeneration of the articular cartilage reduced, there were slight changes in synovial cell growth, granulation and inflammatory cell infiltration, and the proteoglycan content in articular cartilage did not decrease, while in an osteoarthritic model prepared from a normal mouse, there were marked changes in synovial cell growth, granulation and inflammatory cell infiltration. From these findings, we have now found that the GC-B activator possesses anti-arthritis effect as well as assimilating action on the articular cartilage.

Therefore, the present invention comprises the following inventions.

In a first aspect, the present invention provides a therapeutic or prophylactic agent for arthritis comprising a guanyl cyclase B (GC-B) activator as an active ingredient.

In one embodiment of the present invention, the arthritis is osteoarthritis.

In another embodiment of the present invention, the osteoarthritis is osteoarthritis of weight-bearing or non-weight-bearing joints.

In another embodiment of the present invention, the osteoarthritis is degenerative gonarthrosis.

In another embodiment of the present invention, the osteoarthritis is degenerative coxarthrosis.

In another embodiment of the present invention, the osteoarthritis is temporomandibular arthrosis.

In another embodiment of the present invention, the arthritis is caused by rheumatoid arthritis.

In another embodiment of the present invention, the arthritis is caused by osteoarthritis.

In another embodiment of the present invention, the GC-B activator is a type C natriuretic peptide (CNP) or a derivative thereof.

In another embodiment of the present invention, the CNP described above is selected from CNP-22 and CNP-53 from mammals, including human, or birds.

In another embodiment of the present invention, the CNP is CNP-22 of SEQ ID NO:1 or CNP-53 of SEQ ID NO:2.

In another embodiment of the present invention, the CNP derivative has a deletion, substitution or addition of one or several amino acids in the amino acid sequence of SEQ ID NO:1 or SEQ ID NO:2, while possessing a CNP activity.

In another embodiment of the present invention, the therapeutic or prophylactic agent for arthritis further comprises at least one nonsteroidal anti-inflammatory drug.

In a second aspect, the present invention provides an agent for promoting the growth of articular chondrocyte, comprising a GC-B activator as an active ingredient.

In one embodiment of the present invention, the GC-B activator is a CNP or a derivative thereof.

In another embodiment of the present invention, the CNP is CNP-22 or CNP-53 from mammals, including human, or birds.

In another embodiment of the present invention, the CNP is CNP-22 of SEQ ID NO:1 or CNP-53 of SEQ ID NO:2.

In another embodiment of the present invention, the CNP derivative has a deletion, substitution or addition of one or several amino acids in the amino acid sequence of SEQ ID NO:1 or SEQ ID NO:2, while possessing a CNP activity.

In another embodiment of the present invention, the agent for promoting the growth of articular chondrocyte further comprises at least one nonsteroidal anti-inflammatory drug.

In a third aspect, the present invention provides a method for inhibiting arthritis, wherein the arthritis is inhibited by activating GC-B.

In one embodiment of the present invention, the GC-B is activated by a CNP or a derivative thereof.

In another embodiment of the present invention, the CNP is CNP-22 or CNP-53 derived from mammals, including human, or birds.

In another embodiment of the present invention, the CNP is CNP-22 of SEQ ID NO:1 or CNP-53 of SEQ ID NO:2.

In another embodiment of the present invention, the CNP derivative has a deletion, substitution or addition of one or several amino acids in the amino acid sequence of SEQ ID NO:1 or SEQ ID NO:2, while possessing a CNP activity.

In another embodiment of the present invention, the GC-B is activated by a combination of a CNP or a derivative thereof and at least one nonsteroidal anti-inflammatory drug.

In a fourth aspect, the present invention provides a method for promoting the growth of articular chondrocyte, wherein the growth is promoted by activating GC-B.

In one embodiment of the present invention, the GC-B is activated by a CNP or a derivative thereof.

In another embodiment of the present invention, the CNP is CNP-22 or CNP-53 derived from mammals, including human, or birds.

In another embodiment of the present invention, the CNP described above is CNP-22 of SEQ ID NO:1 or CNP-53 of SEQ ID NO:2.

In another embodiment of the present invention, the derivative described above has deletion, substitution or addition of one or several amino acids in the amino acid sequence of SEQ ID NO:1 or SEQ ID NO:2, and has CNP activity.

In another embodiment of the present invention, the GC-B is activated by a combination of a CNP or a derivative thereof and at least one nonsteroidal anti-inflammatory drug.

In a fifth aspect, the present invention provides a method for screening of an agent for promoting the growth of articular chondrocyte, comprising screening candidate agents for the ability to promote the growth of articular chondrocyte using GC-B activity as an indication.

In one embodiment of the present invention, the method comprises preparing cultured cells that express GC-B or cells from articular chondrocytes, culturing the cells in the presence of a candidate agent, and screening of the candidate agents for the ability to promote the growth of articular chondrocyte using the cellular GC-B activity as an indication.

In another embodiment of the present invention, the GC-B activity is determined as an amount of intracellular cGMP produced.

In another embodiment of the present invention, the method comprises preparing a cultured cell line which has been forced to express GC-B, culturing the cell line in the presence or absence of a candidate agent, determining the amount of produced intracellular cGMP, and screening the candidate agents for the ability to promote the growth of articular chondrocyte using as an indication the difference between the amounts of intracellular cGMP produced in the presence and absence of the candidate agent.

In a sixth aspect, the present invention provides a method for screening a therapeutic agent for osteoarthritis, rheumatoid arthritis or arthritis comprising screening a candidate agent for osteoarthritis, rheumatoid arthritis or arthritis using GC-B activity as an indication.

In one embodiment of the present invention, the method comprises preparing cultured cells that express GC-B, or cells from articular chondrocytes, culturing the cells in the presence of a candidate agent, and screening the candidate agent for an agent capable of treating osteoarthritis, rheumatoid arthritis or other arthritis using the cellular GC-B activity as an indication.

In another embodiment of the present invention, the GC-B activity is determined as an amount of intracellular cGMP produced.

In another embodiment of the present invention, the method comprises preparing a cultured cell line which has been forced to express GC-B, culturing the cell line in the presence or absence of a candidate agent, determining the amount of intracellular cGMP produced, and screening of the candidate agent for an agent capable of treating osteoarthritis, rheumatoid arthritis or other arthritis using as an indication the difference between the amounts of intracellular cGMP produced in the presence and absence of the candidate agent.

In a seventh aspect, the present invention provides a therapeutic or prophylactic agent for osteoarthritis comprising a GC-B activator as an active ingredient.

In one embodiment of the present invention, the therapeutic or prophylactic agent for osteoarthritis described above further comprises at least one nonsteroidal anti-inflammatory drug.

In an eighth aspect, the present invention provides a therapeutic or prophylactic agent for rheumatoid arthritis comprising a GC-B activator as an active ingredient.

In one embodiment of the present invention, the therapeutic or prophylactic agent for rheumatoid arthritis further comprises at least one nonsteroidal anti-inflammatory drug.

In a ninth aspect, the present invention provides an activation promoter for a guanyl cyclase B (GC-B) activator, comprising a nonsteroidal activator.

In one embodiment of the present invention, the GC-B activator is a CNP or a derivative thereof.

In another embodiment of the present invention, the CNP is selected from CNP-22 and CNP-53 derived from mammals, including human, or birds.

In another embodiment of the present invention, the CNP is CNP-22 of SEQ ID NO:1 or CNP-53 of SEQ ID NO:2.

In another embodiment of the present invention, the CNP derivative has a deletion, substitution or addition of one or several amino acids in the amino acid sequence of SEQ ID NO:1 or SEQ ID NO:2, while possessing a CNP activity.

In another embodiment of the present invention, the nonsteroidal activator is a cyclooxygenase inhibitor.

In another embodiment of the present invention, the cyclooxygenase inhibitor is selected from the group consisting of indomethacin, ibuprofen, piroxicam, salicylic acid, diclofenac, ketoprofen, naproxen and piroxicam.

In a tenth aspect, the present invention further provides a method for activating a GC-B activator, wherein the activation promoter as described above is used.

The specification of this application encompasses the contents as disclosed in the specification and/or drawings of Japanese Patent Application No. 2004-107924, which is claimed as a priority of the application.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1 shows the construction of a vector for preparing a CNP transgenic mouse. FIG. 1A: cDNA of the mouse CNP, which has been incorporated into pGEM-T Easy vector, was cut out with Pst I and blunt-ended at each end. FIG. 1B: pSG1 was treated with EcoR I and blunt-ended. FIG. 1C: The mouse CNP cDNA prepared in FIG. 1A was incorporated into the pSG1 obtained in FIG. 1B.

FIG. 11 is a graph showing the inhibitory effect of CNP-22 (6 ng/day, continuous subcutaneous administration), indomethacin (Indo., 1 mg/kg, oral administration) and a combination thereof on the knee joint swelling in a C57BL/6 J Jc1 collagenase OA mouse model.

FIG. 12 is a graph showing the effectiveness of CNP-22 for arthritis in the limb ends and body weight change in an adjuvant arthritis rat model.

DETAILED DESCRIPTION OF THE INVENTION

The present invention is further described with reference to the figures.

Figure 3:
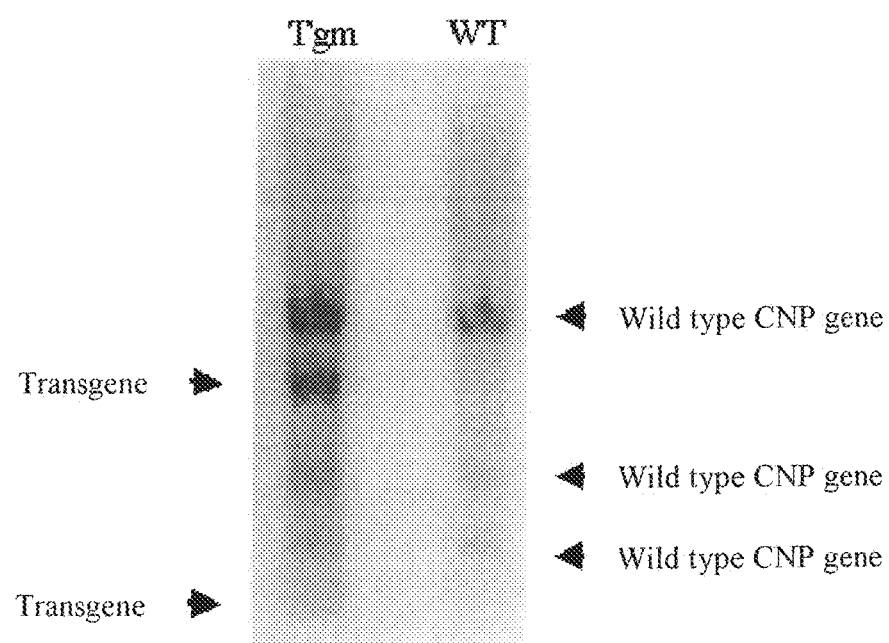
FIG. 3 shows the results of a genotypical analysis of a CNP transgenic mouse. In the wild type mouse (WT) 3 signals (indicated as "Wild type CNP gene") were detected, while in the transgenic mouse (Tgm) 2 signals (indicated as "Transgene") derived from the transgene were detected in addition to the wild-type CNP gene.

We analyzed the genotype of a CNP-transgenic mouse (CNP Tgm) produced as described later in Example 2 using Southern blotting. As a result, we detected 3 signals ("Wild type CNP gene") in the wild type mouse, while detecting 2 signals ("Transgene") derived from the transgene in the CNP Tgm in addition to the wild-type CNP gene, as shown in FIG. 3. The CNP levels in the liver, an organ expected to highly express said transgene, and in blood plasma were determined in order to study the expression of CNP in the CNP Tgm. As a result, it was found that the CNP Tgm showed about 10 fold and about 24 fold higher. CNP levels in the liver and blood plasma, respectively, than the wild type, demonstrating statistically significant overexpression of CNP peptides (Table 1 in Example 4).

Furthermore, the thickness of the articular cartilage and the number of chondrocytes were examined histologically to carry out a histological analysis of the CNPTgm's articular cartilage, and the results indicated that the articular cartilage was statistically significantly thick (FIG. 4) and the number of articular chondrocytes was statistically significantly large (FIG. 5) in the CNPTgm. These results showed that GC-B activators such as CNP may increase the thickness of the articular cartilage by increasing the number of chondrocytes.

Figure 6A:
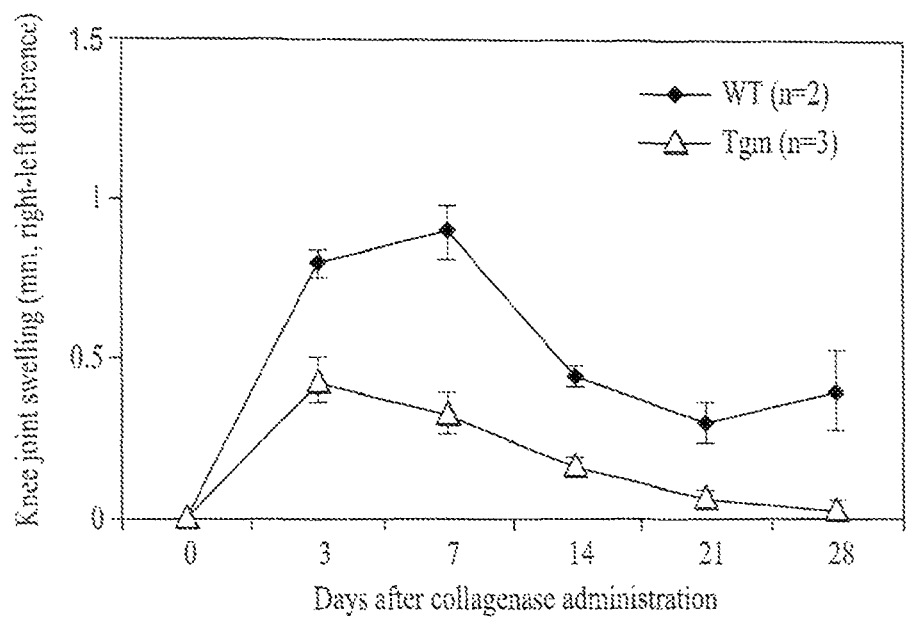
FIG. 6 is a graph showing resistance to articular swelling in a collagenase induced OA model in CNP transgenic mice. After administering 3% collagenase or physiological saline to a CNP transgenic mouse (Tgm) and a wild-type mouse (WT) into the right knee joint, the width of bilateral knee joints was measured and the difference in the width was used as an indication for knee joint swelling to evaluate progress (FIG. 6A) and the area under the curve (AUC) (FIG. 6B). The CNP transgenic mouse tended to have weak swelling in the right knee joint, and had a significantly smaller AUC than that in the wild type. **: p<0.01, N.S.: not significant. Unpaired Student's t-test.
Figure 6B:
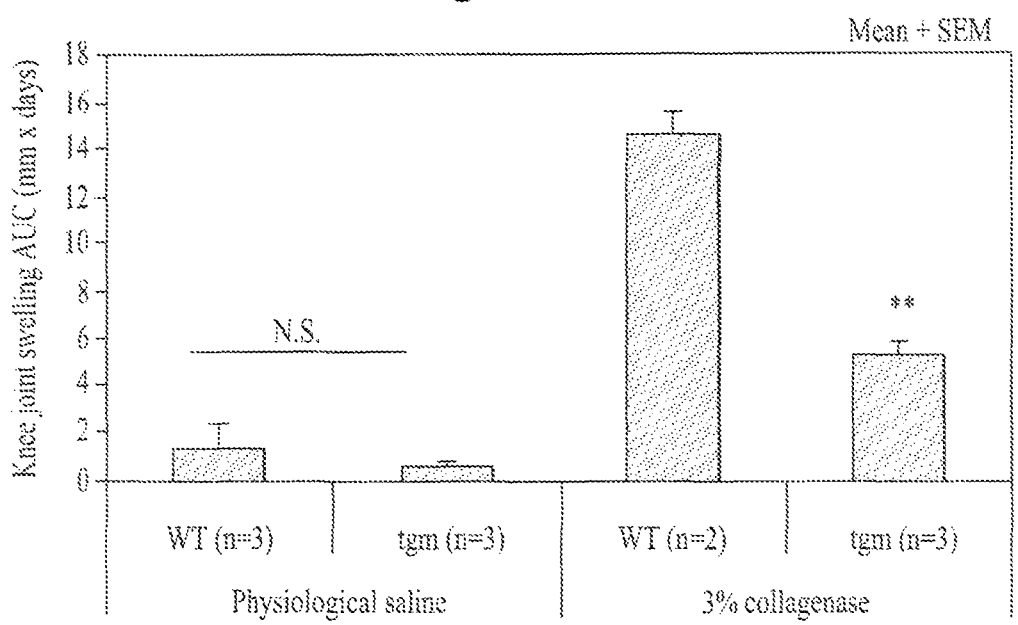
Figure 7A:
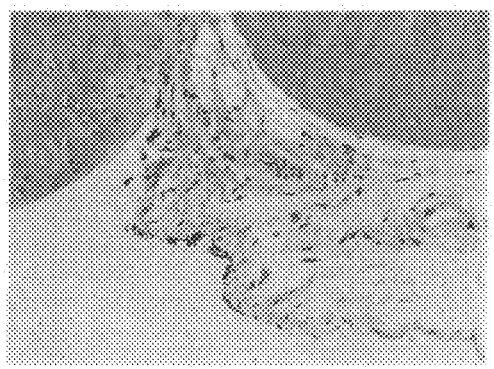
FIG. 7A is a view of normal synovial tissue.
Figure 7B:
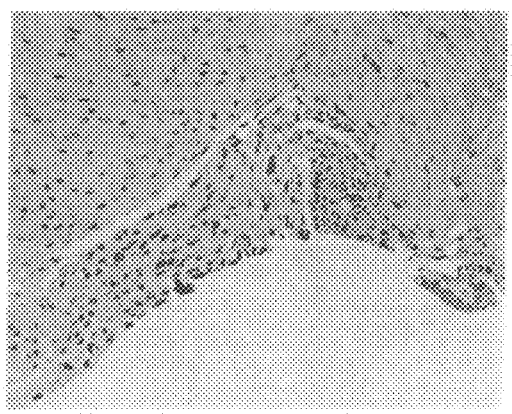
FIG. 7 shows histological changes in the right knee joint synovial membrane in a collagenase OA model. It is a histological image of the right knee joint synovial membrane 28 days after administration of 3% collagenase physiological saline to a CNP transgenic mouse and a wild-type mouse into the right knee joint. When administered 3% collagenase, the wild type mouse showed hyperplasia of synovial epithelial cells, granulation and inflammatory cell infiltration (FIG. 7B). On the other hand, these findings were very few in the CNP transgenic mice (FIG. 7C).
Figure 7C:
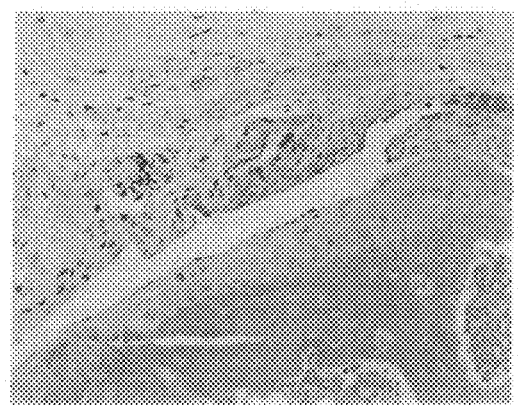
Figure 8A:
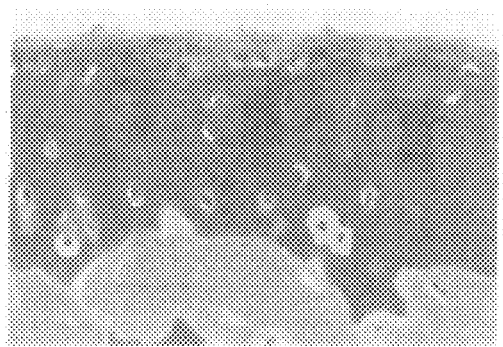
FIG. 8A is a view of normal articular cartilage.
Figure 8B:
FIG. 8 shows histological changes in the articular cartilage of the right medial femoral condyle in a collagenase OA model. It is a histological image of the right medial femoral condyle 28 days after administration of 3% collagenase physiological saline into the right knee joint of a CNP transgenic mouse and a wild-type mouse. The safranine O stainability of the cartilage matrix decreased showing the decreased proteoglycan content in the wild-type mouse (FIG. 8B), while the safranine O stainability was retained in the CNP transgenic mouse (FIG. 8C).
Figure 8C:
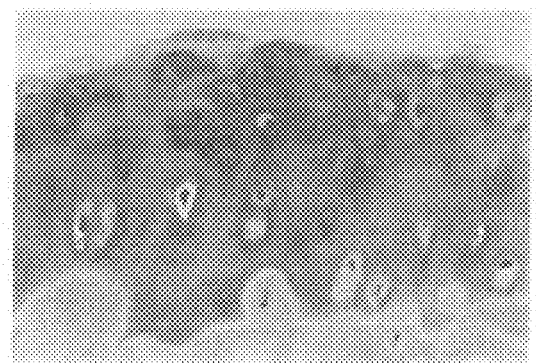

In Example 6 described later, an osteoarthritic animal model was created by injecting collagenase into the knee joint of a mouse to destabilize the knee joint ligament and meniscus and inducing osteoarthritis (Am. J. Pathol. 1989; 135: 1001-14). Osteoarthritic animal models derived from the CNPTgm and a normal mouse were used to evaluate the CNPTgm's resistance to arthritis and articular cartilage degeneration. In the animal model derived from the CNPTgm, when compared to the animal model derived from a normal mouse, the knee joint swelling was significantly milder, articular cartilage degeneration was inhibited to a significantly larger degree, the changes in synovial cell growth, granulation and inflammatory cell infiltration in the synovial membrane were quite slight, and there was almost no change in the proteoglycan content in the articular cartilage (FIGS. 6-8). These results indicated that GC-B activators have inhibitory effect on arthritis and degeneration of the articular cartilage in osteoarthritis.

Figure 9:
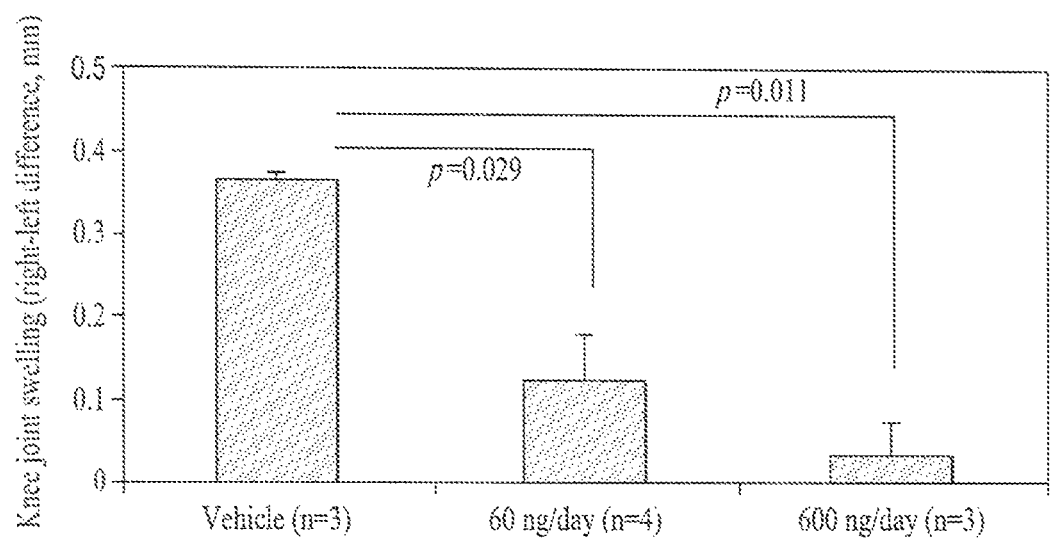
FIG. 9 is a graph showing the effectiveness in inhibiting articular swelling in a CNP collagenase OA mouse model receiving infusion. The graph shows the swelling of the right knee joint as measured 6 days following administration of 1.5% collagenase containing physiological saline into the right knee joint of a C57BL/6 J Jc1 mouse receiving continuous subcutaneous administration of CNP-22. CNP-22, both at 60 and 600 ng/day, significantly inhibited the swelling of the right knee joint as compared to the solvent control group (vehicle). Unpaired Student's t-test.

Furthermore, an osteoarthritic model was created using a normal mouse transplanted with an osmotic pump to examine the therapeutic effect of CNP infusion on the osteoarthritic model. In the CNP group, the animals were found to be resistant to knee joint swelling, have significantly reduced degeneration of the articular cartilage, and show quite mild changes in synovial cell growth, granulation and inflammatory cell infiltration in the synovial membrane (FIG. 9). These results indicated that GC-B activators have a therapeutic effect on osteoarthritis.

Figure 10:
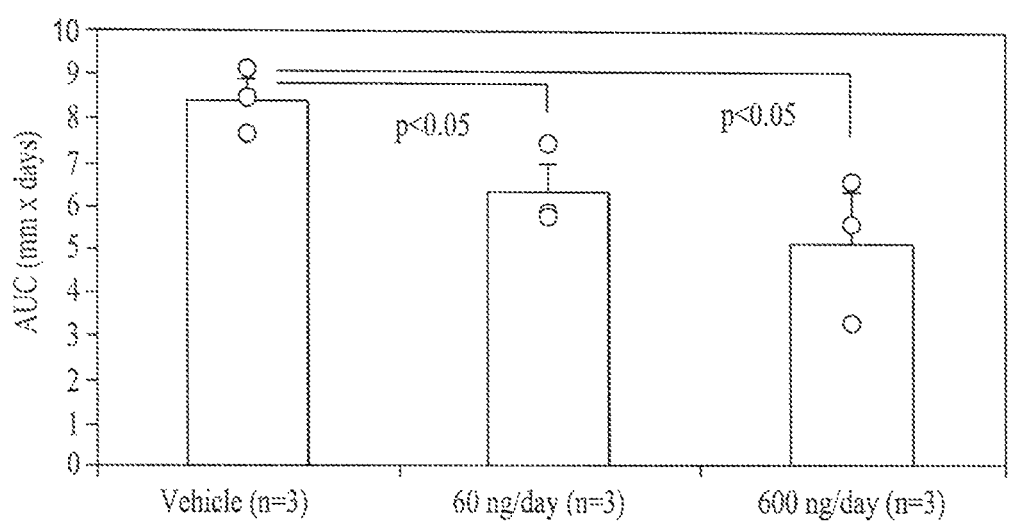
FIG. 10 is a graph showing the effectiveness of CNP infusion in inhibiting articular swelling in a surgical OA mouse model. A C57BL/6 J Jc1 mouse was given continuous subcutaneous administration of CNP-22 and subjected to the surgical procedures of anterocrucial ligament excision, tibial collateral ligament excision and medial meniscus total resection in the right knee joint to induce osteoarthritis. The width of the right and left knee joints was measured 4, 8 and 11 days postoperatively, and the AUC of the difference was shown. CNP-22, both at 60 and 600 ng/day, significantly inhibited the swelling of the right knee joint compared to the solvent control group (vehicle). Unpaired Student's t-test.

Furthermore, a normal mouse transplanted with an osmotic pump was subjected to the surgical procedures of anterocrucial ligament cut, tibial collateral ligament cut and medial meniscus total resection in the right knee joint to induce osteoarthritis, and the therapeutic effect of CNP infusion on the osteoarthritic model was examined. Results showed that the AUC (area under the curve) was significantly lower in the CNP group at either dose compared to the solvent control group (FIG. 10). The results indicated that GC-B activators are also effective in inhibiting arthritis in osteoarthritis induced by physical overload resulting from surgical procedures.

Figure 11A:
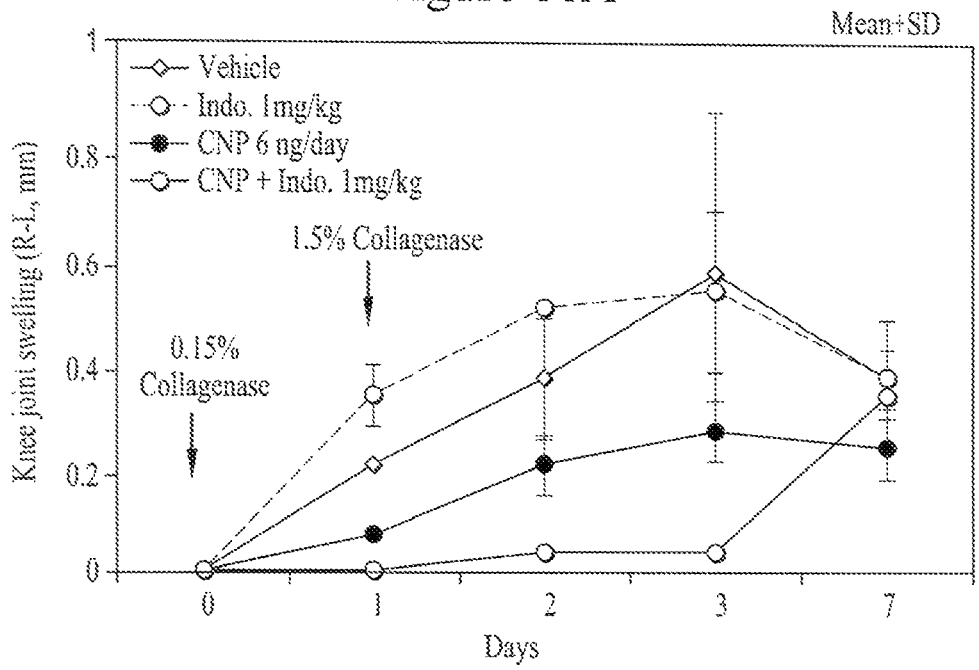
FIG. 11A shows the changes in swelling of the right knee joint over seven days after administration of 0.15% and 1.5% collagenase physiological saline into the mouse right knee joint
Figure 11B:
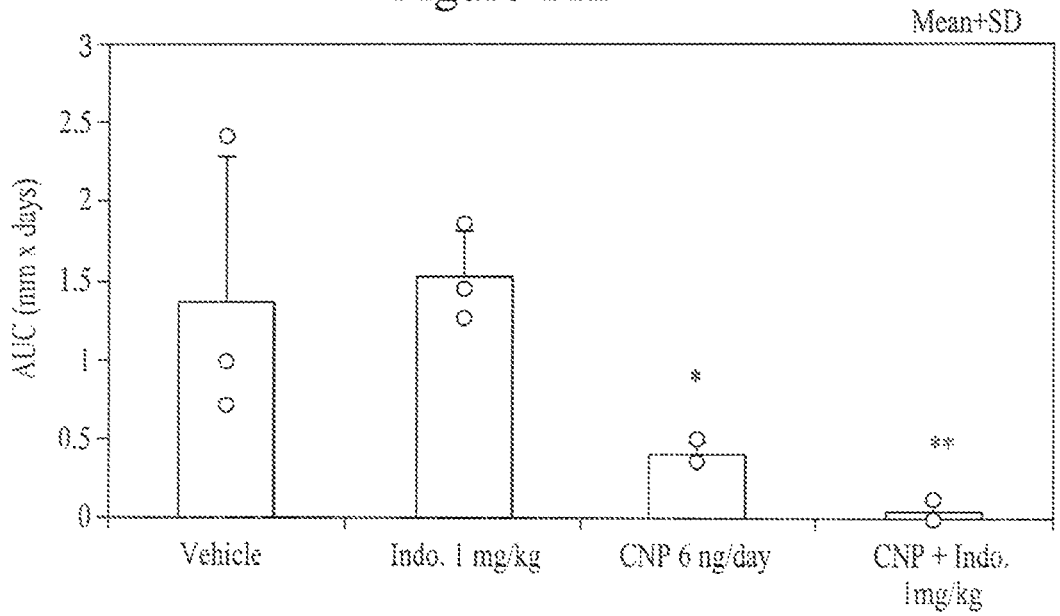
FIG. 11B shows the area under the curve (AUC) of the graph in FIG. 11A. When the AUC was compared, CNP-22 significantly inhibited the swelling of the right knee joint compared to the solvent control group (vehicle) while indomethacin did not. On the other hand, a combination of CNP-22 and indomethacin showed remarkable inhibition, which was significantly stronger than CNP-22 used alone. Unpaired Student's t-test. *: p<0.05 (vs. vehicle), **: p<0.01 (vs. vehicle).

Furthermore, when CNP was administered to a collagenase OA mouse model, either alone or in combination with a nonsteroidal anti-inflammatory drug (NSAID), CNP used alone significantly inhibited knee joint swelling while NSAID used alone did not, and the combination of CNP and NSAID showed an even stronger synergistic anti-swelling effect (Example 9, FIG. 11).

Furthermore, when the effect of CNP was further examined using adjuvant arthritis and collagen arthritis models generally used in laboratories as a rheumatoid arthritis (RA) model (Arthritis & Rheumatism, 27:797-806, 1984; British Journal of Rheumatology, 33:798-807, 1994), the CNP group (rat) showed significantly reduced arthritis and a larger weight gain compared to control, indicating a significant improvement in general condition (Examples 10 and 11 and FIGS. 12 and 13). These results show the effectiveness of CNP for arthritis in rheumatoid arthritis.

From these demonstrative examples, we have now found that, without being restricted by any particular theory or experiment, GC-B activators such as CNP possess anti-arthritis effect as well as assimilating action on the articular cartilage.

Thus, the present invention provides a therapeutic or prophylactic agent for arthritis comprising a GC-B activator as an active ingredient.

Examples of arthritis that can be treated or prevented according to the present invention include, but not limited to, those involving articular cartilage in particular, such as arthritis associated with osteoarthritis, synovitis, rheumatoid arthritis (rheumatoid arthritis (adults) and juvenile rheumatoid arthritis (children)), osteoarthritis, systemic lupus erythematodes (SLE), gout, scleroderma, psoriasis (psoriatic arthritis), mycotic infection such as blastomycosis, ankylosing spondilitis, Reiter's syndrome, septic arthritis, adult Still disease, tertiary Lyme disease (late stage), tuberculosis (tuberculous arthritis), viral infection (viral arthritis), and arthritis caused by infection with gonorrhea (gonococcal arthritis) and bacteria (non-gonococcal bacterial arthritis).

In one embodiment of the present invention, a preferred arthritis is osteoarthritis, or arthritis associated with osteoarthritis.

Osteoarthritis is a disease caused by the degeneration and destruction of the articular cartilage, and examples of applicable osteoarthritis include, for example, (1) osteoarthritis of weight-bearing joints, such as gonarthrosis in the knee joint, coxarthrosis in the hip joint, foot osteoarthritis in the foot and spinal osteoarthritis in the spine, and (2) osteoarthritis of non-weight-bearing joints, such as shoulder osteoarthritis in the shoulder, elbow osteoarthritis in the elbow, hand osteoarthritis in the hand (for example, Heberden's nodes, Bouchard's nodes, thumb CM osteoarthritis) and temporomandibular arthrosis in the jaw.

In one embodiment of the present invention, the osteoarthritis is osteoarthritis affecting weight-bearing joints, preferably gonarthrosis or coxarthrosis.

In another embodiment of the present invention, the osteoarthritis is osteoarthritis affecting non-weight-bearing joints, preferably temporomandibular arthrosis.

Therapeutic or prophylactic agents of the present invention can also be applied in the treatment or prevention of rheumatoid arthritis. Rheumatoid arthritis is thought to be an autoimmune disease, and although it has different etiology from osteoarthritis, it involves, as with osteoarthritis, the degeneration of the articular cartilage surfaces and the destruction of cartilage as it progresses. Consequently, therapeutic agents of the present invention may be administered to inhibit or relieve arthritis.

The terms "treatment," "method for treating" and "therapeutic agent," as used herein, mean eliminating, inhibiting or relieving the symptoms of a patient with arthritis according to the present invention, or methods or drugs for that purpose. In addition, the terms "prevention" and "prophylactic agent" mean preventing arthritis or drugs for that purpose.

As used in the invention, the term "guanyl cyclase B (GC-B)" has the same meaning as natriuretic peptide receptor B (NPR-B).

As used in the invention, the term "activity of GC-B" has the same meaning as guanyl cyclase activity. In the present invention, a guanyl cyclase B (GC-B) activator or GC-B activator is a peptide or a nonpeptidic low-molecular-weight compound, preferably a CNP peptide or a derivative thereof, that can bind to and activate GC-B, which is known as a CNP receptor. Peptides as used herein refer to a substance consisting of amide bond linkages of a plurality of (L-, D- and/or modified) amino acids, and include polypeptides and proteins. A GC-B activator can be identified, for example, by expressing a GC-B receptor in a cultured cell line such as COS-7, adding a candidate agent to the medium, culturing the cell line for a certain time period at a certain temperature (for example, 37° C., 5 minutes), and measuring the amount of intracellular cGMP produced (Science 1991, 252: 120-123). Using such an assay system, and using the amount of intracellular cGMP production as an indication, a GC-B activator may be identified and used in the present invention.

According to one embodiment of the invention, the GC-B activator is a peptide, and preferably CNP or a derivative thereof. Preferred CNP is selected from CNP-22 and CNP-53 from mammals, including human, or birds, and more preferably CNP-22 of SEQ ID NO: 1 or CNP-53 of SEQ ID NO: 2.

According to another embodiment of the invention, the CNP derivative as described above has a deletion, substitution or addition of one or several amino acids in the amino acid sequence of SEQ ID NO: 1 or SEQ ID NO: 2, while possessing a CNP activity. Alternatively, the CNP derivative comprises a sequence having about 70% or more, about 80% or more, about 85% or more, about 90% or more, about 95% or more, about 97% or more, about 98% or more, or about 99% or more identity with the amino acid sequence of SEQ ID NO: 1 or SEQ ID NO: 2 and retains CNP activity.

The term "one or several" as used herein generally represents any integer between 1 and 10, preferably between 1 and 5, more preferably between 1 and 3. The "% identity" between two amino acid sequences may be determined using techniques well known to those skilled in the art, such as BLAST protein search (Altschul, S. F., Gish, W., Miller, W., Myers, E. W. & Lipman, D. J. (1990) "Basic Local Alignment Search Tool" J. Mol. Biol. 215:403-410).

Examples of CNPs usable in the present invention include CNPs from mammals including human (CNP-22: Biochem. Biophys. Res. Commun. 1990; 168: 863-870, International Publication No. WO 91/16342, CNP-53: Biochem. Biophys. Res. Commun. 1990; 170:973-979, Japanese Patent Publication (Kokai) No. 4-74198A (1992), Japanese Patent Publication (Kokai) No. 4-139199A (1992), Japanese Patent Publication (Kokai) No. 4-121190A (1992)), CNPs from birds (Japanese Patent Publication (Kokai) No. 4-120094A (1992)), CNPs from amphibians (Japanese Patent Publication (Kokai) No. 4-120095A (1992)), and CNP derivatives such as CNP analogous peptides disclosed in Japanese Patent Publication (Kokai) No. 6-9688A (1994) and International Publication No. WO 02/074234.

CNP-22 and CNP-53, which consist of 22 and 53 amino residues respectively, are known as naturally occurring CNPs. Because CNPs have a high homology in their sequences between birds and mammals including human, i.e. regardless of the kind of animals, CNPs from birds and mammals including human, preferably CNPs from mammals including human, and more preferably CNPs from human, can be used in the present invention. The amino acid sequence of human CNP-22 or CNP-53 has the sequence shown in SEQ ID NO: 1 or SEQ ID NO: 2 respectively, represented by:
Gly Leu Ser Lys Gly Cys Phe Gly Leu Lys Leu Asp Arg Ile Gly Ser Met Ser Gly Leu Gly Cys (human CNP-22; SEQ ID NO: 1); or
Asp Leu Arg Val Asp Thr Lys Ser Arg Ala Ala Trp Ala Arg Leu Leu Gln Glu His Pro Asn Ala Arg Lys Tyr Lys Gly Ala Asn Lys Lys Gly Leu Ser Lys Gly Cys Phe Gly Leu Lys Leu Asp Arg Ile Gly Ser Met Ser Gly Leu Gly Cys (human CNP-53; SEQ ID NO: 2),
each of which has an intramolecular disulfide bond, i.e. between 6-Cys and 22-Cys in human CNP-22 or between 37-Cys and 53-Cys in human CNP-53, forming a cyclic peptide structure.

Pig CNP-22 and rat CNP-22 have the same amino acid sequence as human CNP-22, whereas the amino acid residues at positions 17 and 28 are His and Gly, respectively, in pig CNP-53 and rat CNP-53, and they are Gln and Ala in human CNP-53, i.e., two amino acids are different in CNP-53 between human and pig or rat (Japanese Patent Publication (Kokai) No. 4-139199A (1992), Japanese Patent Publication (Kokai) No. 4-121190A (1992), and Japanese Patent Publication (Kokai) No. 4-74198A (1992)). In addition, chicken CNP-22 has the same primary structure as human CNP-22, with the exception that the amino acid residue at position 9 is Val (Japanese Patent Publication (Kokai) No. 4-120094A (1992)).

The CNPs usable in the invention include CNPs purified from natural sources, recombinant CNPs produced by known genetic engineering techniques, and CNPs produced by known chemical syntheses (for example, a solid phase synthesis, using peptide synthesizer), preferably human CNP-22 and human CNP-53 produced by genetic engineering techniques. Production of human CNPs by genetic engineering techniques comprises, for example, the steps of incorporating the DNA sequence of human CNP-22 or CNP-53 (Japanese Patent Publication No. 4-139199A (1992)) into a vector such as plasmid or phage, transforming the vector into a procaryotic or eucaryotic host cell, such as E. coli or yeast, and expressing the DNA in suitable culture medium, preferably allowing the cells to secrete the CNP peptide extracellularly, and collecting and purifying the CNP peptide produced. Polymerase chain reaction (PCR) technique can also be used to amplify target DNA.

Basic techniques such as genetic recombination, site-directed mutagenesis and PCR techniques are well-known to those skilled in the art, which are described, for example, in J. Sambrook et al., Molecular Cloning, A Laboratory Manual, Second Edition, Cold Spring Harbor Laboratory Press (1990); Ausubel et al., Current Protocols In Molecular Biology, John Wiley & Sons (1998), and said techniques as disclosed therein may be used for the present invention. As the vectors, commercially available vectors or vectors as disclosed in publications may also be used.

CNP derivatives that may be used in the present invention have the CNP activity and have a cyclic peptide structure having a disulfide bond between two cysteine residues as seen in human CNP-22 or CNP-53. Examples of the CNP derivatives include: fragments of the CNPs as described above; peptides having a substitution of at least one amino acid by another amino acid in the CNPs above or fragments thereof; peptides having a deletion of at least one amino acid in the CNPs above or partial peptides thereof; and peptides having an addition of at least one amino acid in the CNPs above or partial peptides thereof. As used herein, the substitution, deletion or addition of amino acids means that a certain number of amino acids are substituted, deleted or added by a well-known method such as site-directed mutagenesis, with the proviso that the CNP activity is not lost. For example, the CNP-22 or CNP-53 derivatives have a substitution, deletion or addition of one or several amino acids in the amino acid sequence of SEQ ID NO: 1 or SEQ ID NO: 2, possessing the CNP activity.

In general, the substitution of amino acids is preferably a substitution between conservative amino acids. Conservative amino acids may be classified according to, for example, polarity (or hydrophobicity) or types of electric charges. Examples of nonpolar, uncharged amino acids include glycine, alanine, valine, leucine, isoleucine, proline, etc.; aromatic amino acids include phenylalanine, tyrosine and tryptophan; polar, uncharged amino acids include serine, threonine, cysteine, methionine, asparagine, glutamine, etc.; negatively charged amino acids include aspartic acid and glutamic acid; and positively charged amino acids include lysine, arginine and histidine.

In the present invention the CNP activity refers to the activity to act on GC-B to increase guanyl cyclase activity, the activity to eliminate, inhibit or relieve arthritis including osteoarthritis, and the activity to promote the growth of the articular cartilage. The CNP activity can be determined by measuring cellular guanyl cyclase activity, such as, for example, intracellular production of cGMP, and/or by administering a CNP or a derivative thereof for a certain period to mouse or rat models of arthritis, osteoarthritis or rheumatoid arthritis, and measuring as described later in Examples 7 to 10 the effectiveness in inhibiting the arthritis or the degeneration of the articular cartilage.

Examples of CNP-22 analogous peptides include the following cyclic peptides described in Japanese Patent Publication (Kokai) No. 6-9688 (1994) and International Publication No. WO02/074234 (where underlines in the sequences represent variations from human CNP-22).

```
                                              (SEQ ID NO: 3)
Gly Leu Ser Lys Gly Cys Phe Gly Leu Lys Leu Asp
Arg Ile Gly Ala Met Ser Gly Leu Gly Cys (SEQ ID NO: 4)
Gly Leu Ser Lys Gly Cys Phe Gly Leu Lys Leu Asp
Arg Ile Gly Ser Gln Ser Gly Leu Gly Cys (SEQ ID NO: 5)
Gly Leu Ser Lys Gly Cys Phe Gly Leu Lys Leu Asp
Arg Ile Gly Ser Ala Ser Gly Leu Gly Cys (SEQ ID NO: 6)
Cys Phe Gly Leu Lys Leu Asp Arg Ile Gly Ser Met
Ser Gly Leu Gly Cys (SEQ ID NO: 7)
Ser Leu Arg Arg Ser Ser Cys Phe Gly Leu Lys Leu
Asp Arg Ile Gly Ser Met Ser Gly Leu Gly Cys (SEQ ID NO: 8)
Gly Leu Ser Lys Gly Cys Phe Gly Leu Lys Leu Asp
Arg Ile Gly Ser Met Ser Gly Leu Gly Cys Asn Ser
Phe Arg Tyr (SEQ ID NO: 9)
Cys Phe Gly Leu Lys Leu Asp Arg Ile Gly Ser Gln
Ser Gly Leu Gly Cys Asn Ser Phe Arg Tyr (SEQ ID NO: 10)
Cys Phe Gly Xaa Xbb Xcc Asp Arg Ile Gly Xdd Xee
Ser Xff Xgg Gly Cys
(wherein Xaa = Leu, Ile, Val; Xbb = Lys, Leu, Met;
Xcc = Leu, Ile, Ala, Val; Xdd = Ser, Ala, Gly,
Thr, Asn; Xee = Met, Ala, Trp, His, Lys, Ser, Gly;
Xff = Gly, Lys, Ala, Leu; Xgg = Leu, met).
```

In addition, CNP-53 analogous peptides include cyclic peptides containing similar variations of amino acids corresponding to the CNP-22 analogous peptides described above.

The present invention also provides an agent for promoting the growth of articular chondrocyte, comprising a GC-B activator as an active ingredient. This invention is based on the action of a GC-B activator to increase articular chondrocytes. Examples of the GC-B activator are the CNPs as defined above, or derivatives thereof. The CNP is preferably CNP-22 or CNP-53 from mammals, including human, or birds, more preferably CNP-22 of SEQ ID NO:1 or CNP-53 of SEQ ID NO:2. The CNP derivative has deletion, substitution or addition of one or several amino acids in the amino acid sequence of SEQ ID NO:1 or SEQ ID NO:2, and has CNP activity. Other GC-B activators can be identified, for example, by expressing a GC-B receptor in cultured cells such as COS-7, adding a candidate agent to the medium, culturing the cells for a certain time period at a certain temperature (for example, 37° C., 5 minutes), and measuring the amount of intracellular cGMP produced (Science 1991; 252: 120-123). Using such an assay system and using the amount of produced intracellular cGMP as an indication, a GC-B activator may be identified and used for the present invention.

The present invention also provides a method for inhibiting arthritis, wherein the arthritis is inhibited by activating GC-B. The present invention also provides a method for promoting the growth of articular chondrocyte comprising promoting the growth by activating GC-B. These inventions are based on the finding that the arthritis as defined above, preferably osteoarthritis, can be inhibited and the growth of articular chondrocytes can be enhanced by using a GC-B activator, or by activating GC-B. In one embodiment of the present invention, the GC-B is activated by the CNPs as defined above or derivatives thereof.

The present invention further provides a method for screening an agent for promoting the growth of articular chondrocyte, comprising screening candidate agents for the ability to promote the growth of articular chondrocyte using the GC-B activity as an indication. Because GC-B is known to catalyze the synthesis of the second messenger cGMP from GTP through guanyl cyclase activity, the GC-B activity may be determined as the amount of intracellular cGMP produced.

According to an embodiment of the present invention, the screening method as described above may include the steps of preparing cells expressing GC-B, or cells derived from articular chondrocytes, culturing the cells in the presence of a candidate agent, and screening the candidate agent for the ability to promote the growth of articular chondrocyte using the cellular guanyl cyclase activity, for example the amount of intracellular cGMP produced, as an indication.

According to a preferred embodiment of the present invention, the screening method comprises preparing a cultured cell line that had been forced to express GC-B, culturing the cell line in the presence or absence of a candidate agent, determining the amount of intracellular cGMP produced, and screening the candidate agent for the ability to promote the growth of articular chondrocyte using as an indication the difference between the amounts of intracellular cGMP produced in the presence and absence of the candidate agent.

The screening method according to the invention may be used to screen an articular chondrocyte growth promoter by, for example, expressing GC-B in cultured cells such as COS-7, adding a candidate agent to the medium, culturing the cells for a certain time period at a certain temperature (for example, 37° C., 5 minutes), and determining the amount of intracellular cGMP produced (Science 1991; 252: 120-123).

The present invention further provides a method for screening a therapeutic agent for osteoarthritis, rheumatoid arthritis or other arthritis comprising screening candidate agents for an agent capable of treating osteoarthritis, rheumatoid arthritis or other arthritis using GC-B activity as an indication. As described above, the GC-B activity can be determined as guanyl cyclase activity, for example the amount of intracellular cGMP produced.

In one embodiment of the present invention, the screening method as described above may include the steps of: preparing cells that express GC-B, or cells from articular chondrocytes; culturing the cells in the presence of a candidate agent; and screening the candidate agents for an agent capable of treating osteoarthritis, rheumatoid arthritis or other arthritis using the cellular guanyl cyclase activity, for example the amount of intracellular cGMP produced, as an indication.

According to a preferred embodiment of the present invention, the screening method comprises preparing a cultured cell line that had been forced to express GC-B, culturing the cell line in the presence or absence of a candidate agent, determining the amount of intracellular cGMP produced, and screening the candidate agents for an agent capable of treating osteoarthritis, rheumatoid arthritis or arthritis using as an indication the difference between the amounts of intracellular cGMP produced in the presence and absence of the candidate agent.

The screening method according to the invention may be used to screen a therapeutic agent for osteoarthritis, rheumatoid arthritis or other arthritis by, for example, expressing GC-B in cultured cells such as COS-7, adding a candidate agent to the medium, culturing the cells for a certain time period at a certain temperature (for example, 37° C., 5 minutes), and measuring the amount of intracellular cGMP produced (Science 1991; 252: 120-123).

The therapeutic or prophylactic agent of the present invention for arthritis, such as osteoarthritis, is formulated into preparations for oral or parenteral administration by combining the GC-B activator defined above as an active ingredient with a pharmaceutically acceptable carrier, excipient, additive, or the like.

Examples of the carriers and excipients for preparation include lactose, magnesium stearate, starch, talc, gelatin, agar, pectin, gum arabic, olive oil, sesame oil, cacao butter, ethylene glycol, and others conventionally used.

Examples of solid compositions for oral administration include tablets, pills, capsules, powders, granules, and the like. In such solid compositions, at least one active ingredient is mixed with at least one inert diluent, such as lactose, mannitol, glucose, hydroxypropylcellulose, microcrystal cellulose, starch, polyvinylpyrrolidone, magnesium aluminometasilicate, or the like. The composition may, according to a conventional method, also contain additives other than inert diluents, for example, a lubricant such as magnesium stearate, a disintegrating agent such as fibrous calcium glycolate, and a dissolution auxiliary agent such as glutamic acid or aspartic acid. Tablets or pills may, as required, be coated with a glycocalyx, such as sucrose, gelatin or hydroxypropyl methylcellulose phthalate, or with a gastro- or enteric-film, or with two or more layers. Capsules of an absorbable material, such as gelatine, are also included.

Liquid compositions for oral administration may include pharmaceutically acceptable emulsions, solutions, suspensions, syrups and elixirs, and may also contain conventional inert diluents, such as purified water and ethanol. The composition may contain, other than the inert diluent, an adjuvant, such as wetting and suspending agents, a sweetening agent, a flavor, an aromatic, and a preservative.

Examples of parenteral injections include sterile aqueous or non-aqueous solutions, suspensions, and emulsions. Examples of aqueous solutions and suspensions include water for injection and physiological saline for injection. Examples of non-aqueous solutions and suspensions include propylene glycol, polyethylene glycol, vegetable oils such as olive oil, alcohols such as ethanol, and polysorbate 80®. These compositions may further contain adjuvants, such as preservatives, wetting agents, emulsifiers, dispersants, stabilizers (for example, lactose), and dissolution auxiliary agents (e.g., glutamic acid and aspartic acid). The above-described materials may be sterilized by conventional sterilization methods, such as filter sterilization with a microfiltration membrane, heat sterilization such as autoclaving, or incorporation of disinfectants. Injections may be liquid preparations, or freeze-dried preparations that may be reconstituted before use. Examples of excipients for freeze-drying include sugar alcohols and sugars, such as mannitol and glucose.

The therapeutic or prophylactic agent of the present invention is administered by either oral or parenteral administration methods commonly used for pharmaceuticals. Preferred are parenteral administration methods, for example, injection (e.g., subcutaneous, intravenous, intramuscular and intraperitoneal injections), percutaneous administration, trans-mucosal administration (e.g., transnasal and transrectal), and trans-pulmonary administration. Oral administration may also be used.

The dosage of a GC-B activator, preferably a CNP as defined above or a derivative thereof, which is an active ingredient contained in the composition of the present invention, may be determined depending on the type of disease to be treated, the severity of the disease, patient's age, and the like, and may generally range from 0.005 µg/kg to 100 mg/kg, preferably from 0.02 µg/kg to 5 mg/kg., more preferably from 0.02 µg/kg to 0.25 mg/kg. However, the drugs containing CNPs according to the present invention are not limited to these dosages.

The therapeutic or prophylactic agent of the present invention may be combined with conventional or new therapeutic agents, such as anti-inflammatory drugs, hyaluronic acid and adrenocortical steroid, as well as with orthopedic surgical operations, such as arthroscopic surgery, artificial joint replacement and osteotomy.

Combination of an anti-inflammatory drug in particular, for example at least one nonsteroidal anti-inflammatory drug, with a GC-B activator (for example, the CNPs as defined above or derivatives thereof) can provide a synergistic inhibitory effect on arthritis (Example 10).

The "nonsteroidal anti-inflammatory drug" as used herein refers to an anti-inflammatory drug without steroid backbone, and those having the action to inhibit cyclooxygenase enzymes involved in the production of prostaglandins are preferred. Examples of nonsteroidal anti-inflammatory drugs usable in the present invention include, but not limited to, indomethacin (for example, Indacin™); ibuprofen (for example, Brufen™), piroxicam, salicylic acid, diclofenac (for example, Voltaren™), ketoprofen, naproxen, and piroxicam.

Furthermore, the synergistic effect of a combination of the GC-B activator described above with a nonsteroidal anti-inflammatory drug means that, compared to when the GC-B activator is used alone, the activation of GC-B is enhanced, or in other words, the active ingredient of the nonsteroidal anti-inflammatory drug described above serves as an activation promoter in activating GC-B with the GC-B activator.

Thus, the present invention further provides an activation promoter for a GC-B activator, comprising a nonsteroidal activator.

GC-B activators include the CNPs or derivatives thereof as defined above. Examples of CNPs are CNP-22 and CNP-53 from mammals, including human, or birds, more specifically CNP-22 of SEQ ID NO:1 or CNP-53 of SEQ ID NO:2. Examples of the CNP derivatives include those having a deletion, substitution or addition of one or several amino acids in the amino acid sequence of SEQ ID NO:1 or SEQ ID NO:2, and retaining CNP activity.

In the present invention, the nonsteroidal activator as described above is preferably a cyclooxygenase inhibitor. Examples of the cyclooxygenase inhibitor include, but not limited to, indomethacin, ibuprofen, piroxicam, salicylic acid, diclofenac, ketoprofen, naproxen and piroxicam.

The above descriptions of the dosage form, dosage and administration method of the therapeutic and prophylactic agents of the present invention may be applied as is to the activation promoter of the present invention.

The present invention further provides a method for activating a GC-B activator, wherein the activation promoter as described above is used.

The activation promoter and method of the present invention as described above may be used, for example, for treating diseases, such as arthritis, effectively in patient through GC-B activation.

The invention includes, but not limited to, the following items.

(1) A therapeutic or prophylactic agent for arthritis comprising a guanyl cyclase B (GC-B) activator as an active ingredient.

(2) The therapeutic or prophylactic agent according to (1) above, wherein the arthritis is osteoarthritis.

(3) The therapeutic or prophylactic agent according to (2) above, wherein the osteoarthritis is osteoarthritis of weight-bearing or non-weight-bearing joints.

(4) The therapeutic or prophylactic agent according to (3) above, wherein the osteoarthritis is degenerative gonarthrosis.

(5) The therapeutic or prophylactic agent according to (3) above, wherein the osteoarthritis is degenerative coxarthrosis.

(6) The therapeutic or prophylactic agent according to (3) above, wherein the osteoarthritis is temporomandibular arthrosis.

(7) The therapeutic or prophylactic agent according to (1) above, wherein the arthritis is caused by rheumatoid arthritis.

(8) The therapeutic or prophylactic agent according to (1) above, wherein the arthritis is caused by osteoarthritis.

(9) The therapeutic or prophylactic agent according to any of items (1) to (8) above, wherein the GC-B activator is a type C natriuretic peptide (CNP) or a derivative thereof.

(10) The therapeutic or prophylactic agent according to (9) above, wherein the CNP is selected from CNP-22 and CNP-53 derived from mammals, including human, or birds.

(11) The therapeutic or prophylactic agent according to (9) above, wherein the CNP is CNP-22 of SEQ ID NO:1 or CNP-53 of SEQ ID NO:2.

(12) The therapeutic or prophylactic agent according to (9) above, wherein the derivative has deletion, substitution or addition of one or several amino acids in the amino acid sequence of SEQ ID NO:1 or SEQ ID NO:2, and has CNP activity.

(13) The therapeutic or prophylactic agent according to any of items (1) to (12) above, further comprising at least one non-steroidal anti-inflammatory drug.

(14) An agent for promoting the growth of articular chondrocyte comprising a GC-B activator as an active ingredient.

(15) The agent according to (14) above, wherein the GC-B activator is a CNP or a derivative thereof.

(16) The agent according to (15) above, wherein the CNP is CNP-22 or CNP-53 from mammals, including humans, or birds.

(17) The agent according to (15) above, wherein the CNP is CNP-22 of SEQ ID NO:1 or CNP-53 of SEQ ID NO:2.

(18) The agent according to (15) above, wherein the derivative has a deletion, substitution or addition of one or several amino acids in the amino acid sequence of SEQ ID NO:1 or SEQ ID NO:2, while possessing a CNP activity.

(19) The agent according to any of items (14) to (18) above, further comprising at least one nonsteroidal anti-inflammatory drug.

(20) A method for inhibiting arthritis, wherein the arthritis is inhibited by activating GC-B.

(21) The method for inhibition according to (20) above, wherein the GC-B is activated by a CNP or a derivative thereof.

(22) The method for inhibition according to (21) above, wherein the CNP is CNP-22 or CNP-53 from mammals, including human, or birds.

(23) The method for inhibition according to (21) above, wherein the CNP is CNP-22 of SEQ ID NO:1 or CNP-53 of SEQ ID NO:2.

(24) The method for inhibition according to (21) above, wherein the derivative has a deletion, substitution or addition of one or several amino acids in the amino acid sequence of SEQ ID NO:1 or SEQ ID NO:2, while possessing a CNP activity.

(25) The method for inhibition according to any of items (20) to (24) above, wherein the GC-B is activated by a combination of a CNP or a derivative thereof and at least one nonsteroidal anti-inflammatory drug.

(26) A method for promoting the growth of articular chondrocyte, wherein the articular chondrocyte growth is accelerated by activating GC-B.

(27) The method according to (26) above, wherein the GC-B is activated by a CNP or a derivative thereof.

(28) The method according to (27) above, wherein the CNP is CNP-22 or CNP-53 derived from mammals, including human, or birds.

(29) The method according to (27) above, wherein the CNP is CNP-22 of SEQ ID NO:1 or CNP-53 of SEQ ID NO:2.

(30) The method according to (27) above, wherein the derivative has a deletion, substitution or addition of one or several amino acids in the amino acid sequence of SEQ ID NO:1 or SEQ ID NO:2, while possessing a CNP activity.

(31) The method according to any of items (26) to (30) above, wherein the GC-B is activated by a combination of a CNP or a derivative thereof and at least one nonsteroidal anti-inflammatory drug.

(32) A method for screening an articular chondrocyte growth promoter comprising screening a candidate agent for the ability to promote articular chondrocyte using GC-B activity as an indication.

(33) The method according to (32) above, comprising preparing cultured cells that express GC-B, or cells from articular chondrocytes, culturing the cells in the presence of a candidate agent, and screening the candidate agents for the ability to promote the growth of articular chondrocyte using the cell's GC-B activity as an indication.

(34) The method according to (32) or (33) above, wherein the GC-B activity is determined as an amount of intracellular cGMP produced.

(35) The method according to any of items (32) to (34) above, comprising preparing a cultured cell line that had been forced to express GC-B, culturing the cell line in the presence or absence of a candidate agent, determining the amount of intracellular cGMP produced, and screening the candidate agents for the ability to accelerate articular chondrocyte growth using, as an indication, the difference between the amounts of intracellular cGMP produced in the presence and absence of the candidate agent.

(36) A method for screening a therapeutic agent for osteoarthritis, rheumatoid arthritis or other arthritis comprising screening candidate agents for an agent capable of treating osteoarthritis, rheumatoid arthritis or other arthritis using GC-B activity as an indication.

(37) The method according to (36) above, comprising preparing cultured cells that express GC-B, or cells from articular chondrocytes, incubating the cells in the presence of a candidate agent, and screening the candidate agents for an agent capable of treating osteoarthritis, rheumatoid arthritis or other arthritis using the cellular GC-B activity as an indication.

(38) The method according to (36) or (37) above, wherein the GC-B activity is determined as an amount of intracellular cGMP produced.

(39) The method according to any of items (36) to (38) above, comprising preparing a cultured cell line that had been forced to express GC-B, culturing the cell line in the presence or absence of a candidate agent, determining the amount of intracellular cGMP produced, and screening the candidate agents for an agent capable of treating osteoarthritis, rheumatoid arthritis or other arthritis using as an indication the difference between the amounts of intracellular cGMP produced in the presence and absence of the candidate agent.

(40) A therapeutic or prophylactic agent for osteoarthritis comprising a guanyl cyclase B (GC-B) activator as an active ingredient.

(41) The therapeutic or prophylactic agent for osteoarthritis according to (40) above, further comprising at least one nonsteroidal anti-inflammatory drug.

(42) A therapeutic or prophylactic agent for rheumatoid arthritis comprising a guanyl cyclase B (GC-B) activator as an active ingredient.

(43) The therapeutic or prophylactic agent for rheumatoid arthritis according to (42) above, further comprising at least one nonsteroidal anti-inflammatory drug.

(44) A method for treating arthritis comprising administering a GC-B activator to a patient in need of treatment for the arthritis.

(45) The method according to (44) above, wherein the GC-B activator is a CNP or a derivative thereof.

(46) The method according to (44) or (45) above, wherein the arthritis is osteoarthritis.

(47) The method according to (46) above, wherein the osteoarthritis is osteoarthritis of weight-bearing or non-weight-bearing joints.

(48) The method according to (47) above, wherein the osteoarthritis is degenerative gonarthrosis, degenerative coxarthrosis, or temporomandibular arthrosis.

(49) The method according to (44) above, wherein the arthritis is caused by rheumatoid arthritis.

(50) The method according to (44) above, wherein the arthritis is caused by osteoarthritis.

(51) The method according to any of items (45) to (50) above, wherein the CNP is selected from CNP-22 and CNP-53 derived from mammals, including humans, or birds.

(52) The method according to any of items (45) to (50) above, wherein the CNP is CNP-22 of SEQ ID NO:1 or CNP-53 of SEQ ED NO:2.

(53) The method according to any of items (45) to (50) above, wherein the derivative has a deletion, substitution or addition of one or several amino acids in the amino acid sequence of SEQ ID NO:1 or SEQ ID NO:2, while possessing a CNP activity.

(54) The method according to any of items (44) to (53) above, wherein the GC-B activator is contained in combination with at least one nonsteroidal anti-inflammatory drug.

(55) An activation promoter for a GC-B activator, comprising a nonsteroidal activator.

(56) The activation promoter according to (55) above, wherein the GC-B activator is a CNP or a derivative thereof.

(57) The activation promoter according to (56) above, wherein the CNP is selected from CNP-22 and CNP-53 from mammals, including human, or birds.

(58) The activation promoter according to (56) above, wherein the CNP is CNP-22 of SEQ ID NO:1 or CNP-53 of SEQ ID NO:2.

(59) The activation promoter according to (56) above, wherein the derivative has a deletion, substitution or addition of one or several amino acids in the amino acid sequence of SEQ ID NO:1 or SEQ ID NO:2, while possessing a CNP activity.

(60) The activation promoter according to (55) above, wherein the nonsteroidal activator is a cyclooxygenase inhibitor.

(61) The activation promoter according to (60) above, wherein the cyclooxygenase inhibitor is selected from the group consisting of indomethacin, ibuprofen, piroxicam, salicylic acid, diclofenac, ketoprofen, naproxen and piroxicam.

(62) A method for activating a GC-B activator, wherein the activation promoter according to any of (55) to (61) above is used.

The present invention will be described in more detail by the following examples, which are for illustrative purposes only and are not intended to limit the scope of the invention. Thus, the present invention is not limited to those examples.

EXAMPLES

Example 1

Construction of Vector for Preparing CNP Transgenic Mouse

As shown in FIG. 1A, the murine CNP cDNA (526 bp; FEBS Lett. 276:209-213, 1990) was subcloned into pGEM-T easy vector (Promega), and was then cut with Pst I and blunt-ended to prepare a mouse CNP cDNA. The vector PSG 1 (Promega; FIG. 1B) was cut with EcoRI, blunt-ended and ligated with the murine CNP cDNA, as shown in FIG. 1C, to prepare a SAP-mCNP vector (pSG1-CNP).

Example 2

Production of CNP Transgenic Mouse

Figure 2:
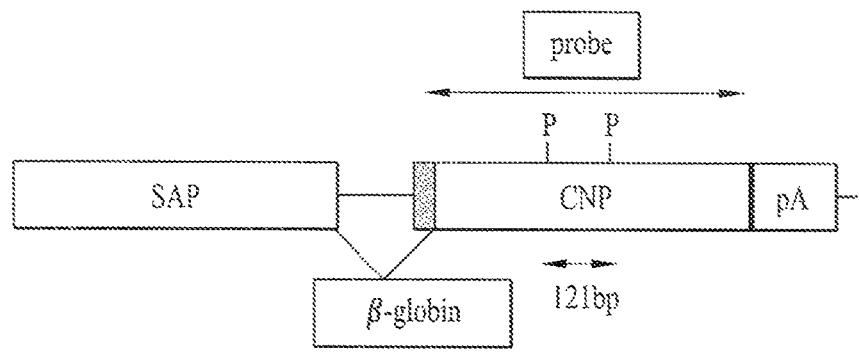
FIG. 2 shows a DNA fragment for injection. A fragment (about 2.3 kb) containing the CNP gene was cut out from pSG1-CNP prepared in FIG. 1C by digesting with Hind III and Xho I, and it was used as a fragment for injection.

A DNA fragment for injection was prepared as follows. The SAP-mCNP vector (pSG1-CNP; FIG. 1C) with an inserted CNP gene was first treated with Hind III and Xho I to cut out a fragment (about 2.3 kb) containing the CNP gene. The fragment was then collected using Gel Extraction Kit (QIAGEN), and was diluted with PBS" at a concentration of 3 ng/µl, thereby obtaining the DNA fragment for injection (FIG. 2).

The mouse egg at pronucleus stage into which the DNA fragment was injected was collected as follows. First, a C57BL/6 female mouse (Clea Japan, Inc.) was injected intraperitoneally with 5 i.u pregnant mare serum gonadotropin (PMSG), and 48 hours later, with 5 i.u human chorionic gonadotropin (hCG), in order to induce superovulation. This female mouse was crossed with a congeneric male mouse. In the next morning of the crossing, in the female mouse the presence of a plug was confirmed and subsequently the oviduct was perfused to collect a mouse egg at pronucleus stage.

The DNA fragment for injection was injected into the pronucleus egg using a micromanipulator (Latest Technology in Gene Targeting (Yodosha, Japan), 190-207, 2000). Specifically, the DNA fragment was injected into 660 C57BL/6J embryos, and on the following day, 561 embryos at 2-cell stage were transplanted into the oviducts of recipient females on day 1 of false pregnancy at about 10 per each side of the oviduct (about 20/animal).

Recipient females, which had not been delivered of offsprings by the expected date of delivery, were subjected to cesarean section, resulting in the birth of offsprings which were raised by a foster mother. Total 136 offsprings were obtained, 5 of which were transgenic mice with an introduced CNP gene (hereafter referred to as "Tgm"). Hereinafter, the mouse initially obtained is referred to as the Founder.

All Founder mice were male, and the subsequent generation of offsprings (i.e., F1 mice) were obtained from four of the five lines.

Example 3

Genotype Analysis of CNP Transgenic Mouse

Genotype analysis was performed by Southern blotting according to procedures as described below.

The tail (about 15 mm) was taken from the 3-week old mouse and treated with proteinase K (at 55° C., with shaking at 100 rpm over day and night) to obtain a lysis solution. The obtained solution was then subjected to an automated nucleic acid separator (KURABO NA-1000; Kurabo, Japan) to prepare genomic DNA. The genomic DNA (15 μg) was treated with Pvu II (200 U), then with phenol-chloroform to remove the restriction enzyme, and was precipitated with ethanol to collect the DNA. The obtained DNA was dissolved in 25 μL of TE and subjected to electrophoresis on 0.7% agarose gel (at 50V constant voltage), then the gel was treated with 0.25M HCl solution for 15 minutes to cleave the DNA, washed with water, and blotted overnight onto a nylon membrane in 0.4M NaOH solution. Thereafter, the DNA on the membrane was fixed by the UV crosslink method. The membrane was treated (at 42° C. for 2 hours) with a hybridization solution (50% formamide, 0.5×Denhardt's, 0.5% SDS, 5×SSPE), and a $^{32}$P labeled probe, which has been prepared with BcaBEST Labeling Kit (TaKaRa, Japan) using the CNP cDNA (about 0.5 kb) as a template, was added to the membrane for hybridization at 42° C. overnight. After treatment with a detergent solution (2×SSC, 0.1% SDS) at 55° C. for 20 minutes, the membrane was exposed to an Imaging Plate (Fuji Film) overnight to detect signals of the transgene using BAS2000 (Fuji Film, Japan) (FIG. 3). In the wild-type mouse (WT) 3 signals (wild-type CNP gene) were detected, while in the transgenic mouse (Tgm) 2 signals (transgene) derived from the transgene were detected in addition to the wild-type CNP gene.

Example 4

CNP Expression in CNP Transgenic Mouse

A CNP-22 EIA measuring kit (PHOENIX PHARMACEUTICALS INC.) was used for the determination of a CNP level.

Three each of 7-week old male and female CNP transgenic mice, as well as 3 each of male and female normal litter of mice, were euthanized by exsanguination from the postcava under ether anesthesia.

The liver, which is an organ expected to exhibit high expression of the transgene, was removed, and the EIA assay buffer from the measuring kit as above was added at 1 ml per 0.1 g of liver weight, followed by cooling on ice. The liver was homogenized in a Waring blender (Physcotron), and after centrifugation (at 2,000 rpm for 5 minutes), the supernatant was used as a sample for the determination of CNP-22 levels.

One mg of ethylenediaminetetraacetate-4Na (Junsei Chemical Co., Ltd., Japan) and 2 trypsin-inhibition units of aprotinin (Sigma) were added to the drawn blood and agitated to separate blood plasma, which was used as a sample for the determination of CNP-22 levels.

The results are shown in Table 1.

TABLE 1

CNP expression in CNP transgenic mouse

|  |  | Liver (ng/g tissue) | mean ± SD | Plasma (ng/mL) | mean ± SD |
|---|---|---|---|---|---|
| Wild type | No. 1 | 38.8 | 29.3 ± 20.5 | 0.3 | 0.3 ± 0.06 |
|  | No. 2 | 5.9 |  | 0.4 |  |
|  | No. 3 | 43.3 |  | 0.3 |  |
| CNP tgm | No. 1 | 293.3 | 290 ± 81.7** | 10.3 | 8.0 ± 4.7# |
|  | No. 2 | 370.0 |  | 11.1 |  |
|  | No. 3 | 206.7 |  | 2.6 |  |

**$p < 0.01$ (unpaired Student's t-test)
$p < 0.05$ (Wilcoxon rank sum test)

The CNP transgenic mouse showed about 10 fold and about 24 fold higher CNP-22 level in the liver and blood plasma respectively, than the wild type when the mean±SD values were compared between them. In each case the difference was statistically significant. It was confirmed, from the results, that the CNP peptide was overexpressed in the CNP transgenic mouse.

Example 5

Histological Analysis of the Articular Cartilage of CNP Transgenic Mouse

To perform histological analysis of the articular cartilage for the thickness and the number of chondrocytes, 5 each of 9-week-old female CNP transgenic mice and female normal litter of mice were euthanized by exsanguination from the postcava under ether anesthesia, and the femur was fixed in 20% formalin for a week. After dipping in a 20% aqueous solution of EDTA-4Na (pH 7.4) (Junsei Chemical Co., Ltd., Japan) for decalcification, the facies patellaris femoris was subjected to a midline sagittal section and embedded in paraffin by a conventional method to prepare paraffin blocks. A 4 mm-thick section was further sectioned with a microtome to prepare paraffin sections, which were stained with hematoxylin-eosin stain. For the thickness of the articular cartilage, one microscopicl field observed using an objective lens (×10) was incorporated into an image analysis software (IPAP, Sumika Technoservice, Japan), and the length was measured at five points in the field using the software to calculate an average of the length, which average was used as the thickness of the articular cartilage of the individual. The same field was measured for the number of chondrocytes as well. Mean values and standard deviations for these items were calculated in normal mice and CNP transgenic mice of the same sex (Microsoft Excel 2000, Microsoft), and statistical analysis was performed using the unpaired Student's t-test (SAS ver.6.12, SAS Institute Japan, Japan).

Figure 4:
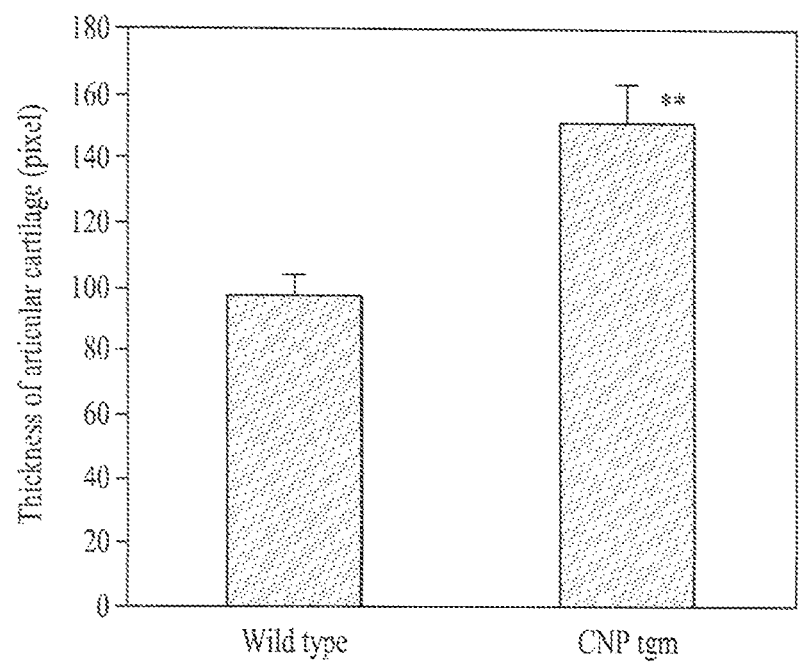
FIG. 4 is a graph showing thickening of the articular cartilage in a CNP transgenic mouse. The thickness of the articular cartilage of facies patellaris femoris was compared between a normal litter (Wild) and CNP transgenic mice (CNP tgm). The figure indicates that CNP transgenic mice have statistically significantly thicker articular cartilage. **: p<0.01, unpaired Student's t-test.
Figure 5:
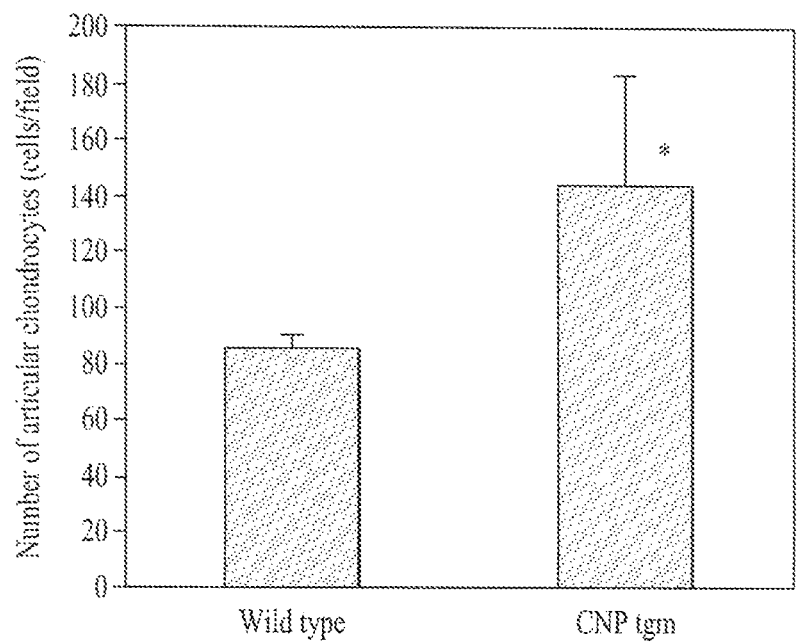
FIG. 5 is a graph showing an increase in the number of articular chondrocytes in a CNP transgenic mouse. The number of chondrocytes per field under the optical microscope in the articular cartilage of facies patellaris femoris was compared between a normal litter (Wild) and CNP transgenic mice (CNP tgm). The figure indicates that CNP transgenic mice have a statistically significantly larger number of chondrocytes per microscopic field. *: p<0.05, unpaired Student's t-test.

CNP transgenic mice, both male and female mice, demonstrated that they had statistically significantly thicker articular cartilage (FIG. 4). In addition, the number of articular chondrocytes per microscopic field was shown to be statistically significantly larger in both male and female CNP transgenic mice (FIG. 5).

These results revealed that GC-B (NPR-B) activating substances such as CNPs can increase the thickness of the articular cartilage by increase of the number of chondrocytes, as well as by increase of the cell volume due to hypertrophy of individual chondrocytes as generally known [J Biol Chem 2003; 278(21): 18824-32].

Example 6

Resistance of CNP Transgenic Mouse to Osteoarthritis Model

An osteoarthritis animal model was created by injecting collagenase into the knee joint to destabilize the knee joint ligament and meniscus (Am. J. Pathol. 1989; 135:1001-14). Resistance to arthritis and articular cartilage degeneration was evaluated in this animal model using a CNP transgenic mouse to confirm the preventive and therapeutic effects of CNPs on osteoarthritis. 6 μl of 3% type II collagenase (Sigma) solution in physiological saline was injected twice (initial dosing day and after 7 days) into the right knee joint of CNP transgenic mice and the litter of wild-type C57BL/6 strain mice. The width of both the right and left knee joints was measured on time with a slide caliper (Mitutoyo Corp., Japan) for 28 days after administration, and the difference between the right and left knee joints was calculated to represent the swelling of knee joints. The area under the time-course curve (AUC) of sequential changes was calculated by the trapezoidal method, and compared by the Student's t-test between the CNP transgenic mouse and the wild-type mouse. The result that the AUC was significantly smaller in the CNP transgenic mouse than in the wild type indicates that the CNP transgenic mouse is resistant to knee joint swelling caused by collagenase (FIG. 6). To perform histopathological evaluation of the arthritis and articular cartilage degeneration, the knee joint was removed following euthanasia by exsanguination under ether anesthesia on day 28 after the administration of collagenase, and hematoxylin-eosin-stained and safranine O-stained samples were prepared as described in Example 5, and analyzed histologically. As a result, the wild-type mouse showed collagenase-induced marked synovial cell growth, granulation and inflammatory cellular infiltration in the synovial membrane while these changes were remarkably reduced in the CNP transgenic mouse (FIG. 7). For the degeneration of the articular cartilage, the wild-type mouse showed decreased safranine stainability and a decreased proteoglycan content in the articular cartilage while these changes were mild in the CNP transgenic mouse, and this provides histopathological evidence that the CNP transgenic mouse is resistant to the degenerative changes in articular cartilage caused by administration of collagenase (FIG. 8). The plasma CNP level as determined using a EIA kit (Phoenix Pharmaceutical) was an average of 0.21 ng/mL in the wild-type mouse and 0.50 ng/mL in the CNP transgenic mouse.

These results revealed that CNPs have inhibitory action on arthritis and degenerative changes in articular cartilage in osteoarthritis.

Example 7

Therapeutic Effect of CNP Infusion on Osteoarthritic Model (1)

An osmotic pump (2004 model, Durect) containing the solutions below was transplanted subcutaneously in the back of a 9-week-old male C57BL/6 J strain mouse.
- Solvent: Distilled water containing 5% dextrose (Junsei Chemical Co., Ltd., Japan), 10% mannose (Nacalai Tesque Inc., Japan) and 5 mmol/L hydrochloric acid (Wako Pure Chemical Industries, Japan).
- 10 μg/mL solution (60 ng/day) of CNP-22 (Calbiochem Novabiochem).
- 100 μg/mL solution (600 ng/day) of CNP-22 (Calbiochem Novabiochem.).

Six days after transplantation, 6 μL of 1.5% type II collagenase (Sigma) solution was injected into the right knee joint, the breadth of both the right and left knee joints was measured on time with a slide caliper (Mitutoyo Corp., Japan) for 28 days after injection, and the difference between the right and left knee joints was calculated. This difference represented the swelling of knee joints, and the AUC was compared between the solvent control and CNP groups by the Student's t-test (SAS ver. 6.12). Results showed that the AUC value was significantly lower in the CNP-22 group at either dose compared to the solvent control group. Hematoxylin-eosin-stained and safranin O-stained samples were prepared according to the method as described in Example 5, and analyzed histopathologically.

As a result, the solvent control group showed collagenase-induced marked synovial cell growth, granulation and inflammatory cell infiltration in the synovial membrane while these changes were remarkably reduced in the CNP group (FIG. 9). These results from synovial tissues revealed that CNPs have a therapeutic effect on osteoarthritis.

Example 8

Therapeutic Effect of CNP Infusion on Osteoarthritic Model (2)

An osmotic pump (2004 model, Durect) containing the solutions below was transplanted subcutaneously in the back of a 9-week-old male C57BL/6 J strain mouse (CLEA Japan, Japan).
- Solvent: Distilled water containing 5% dextrose (Junsei Chemical Co., Ltd., Japan), 10% mannose (Nacalai Tesque Inc., Japan) and 5 mmol/L hydrochloric acid (Wako Pure Chemical Industries, Japan).
- 10 mg/mL solution (60 ng/day) of CNP-22 (Calbiochem Novabiochem).
- 100 mg/mL solution (600 ng/day) of CNP-22 (Calbiochem Novabiochem).

On the following day of transplantation, the mouse was anesthetized with ether and subjected to the surgical procedures of anterocrucial ligament excision, medial collateral ligament excision and medial meniscus total resection in the right knee joint to induce osteoarthritis. The breadth of both the right and left knee joints was measured on time with a slide caliper (Mitutoyo Corp.) for 11 days after administration, and the difference between the right and left knee joints was calculated. This difference represented the swelling of knee joints, and the AUC was compared between the solvent control and CNP groups by the Student's t-test (SAS Preclinical Package, SAS Institute Japan, Japan). Results showed that the AUC value was significantly lower in the CNP-22 group at either dose compared to the solvent control group (FIG. 10).

The results revealed that CNPs are also effective in inhibiting arthritis in osteoarthritis caused by physical overload on the knee joint resulting from surgical procedures.

Example 9

Combined Effect of Nonsteroidal Anti-Inflammatory Drug (NSAID) and CNP in Collagenase OA Model An osmotic primp (2004 model, Durect) containing the solutions below was transplanted subcutaneously in the back of a 9-week-old male C57BL/6 J strain mouse.

Solvent: Distilled water containing 5% dextrose (Junsei Chemical Co., Ltd., Japan), 10% mannose (Nacalai Tesque Inc., Japan) and 5 mmol/L hydrochloric acid (Wako Pure Chemical Industries, Japan).

1 μg/mL solution (6 ng/day) of CNP-22 (Calbiochem Novabiochem).

In addition, to examine the effect of the NSAID indomethacin (Sigma) when used alone and in combination with the CNP, an indomethacin suspension in 0.2% carboxymethyl cellulose (Nacalai Tesque Inc., Japan) was administered orally in a forced manner at 1 mg/kg once a day for 4 successive days from the date of pump transplantation described above.

The experimental groups were set as follows.
Solvent control (infused solvent, orally administered solvent)
CNP 6 ng/day
Indomethacin 1 mg/kg
CNP 6 ng/day+indomethacin 1 mg/kg On the date of pump transplantation and the following day, 6 μL of 0.15% type II collagenase (Sigma) and 6 μL of 1.5% type II collagenase solutions, respectively, were injected into the right knee joint, the breadth of both the right and left knee joints was measured daily with a slide caliper (Mitutoyo Corp., Japan) for 7 days after injection, and the difference between the right and left knee joints was calculated. This difference represented the swelling of knee joints, and the AUC was compared between the solvent control and CNP groups by the Student's t-test (SAS ver. 6.12).

As a result, indomethacin when used alone was not inhibitory for the swelling of knee joints. The group given the CNP at 6 ng/day significantly inhibited the swelling of knee joints. The group given the combination of CNP and indomethacin showed significantly stronger inhibition for the swelling of knee joints compared to the group given the CNP alone (FIG. 11). These results revealed that the CNP when used alone is significantly more effective in inhibiting the swelling of knee joints compared to the NSAID, which is a standard anti-arthritis, and also has a synergistic effect when used in combination with the NSAID.

Example 10

Effect of CNPs on Adjuvant Arthritis Rat Model

An osmotic pump (2004 model, Durect) containing the solutions below was transplanted subcutaneously in the back of a 6-week-old male LEW/Crj strain rat (Charles River Laboratories Japan, Inc., Japan).

Solvent: Distilled water containing 5% dextrose (Junsei Chemical Co., Ltd., Japan), 10% mannose (Nacalai Tesque Inc., Japan) and 5 mmol/L hydrochloric acid (Wako Pure Chemical Industries, Japan).

10 μg/mL solution (60 ng/day) of CNP-22 (Calbiochem Novabiochem).

On the following day of transplantation, powder of killed tuberculosis bacteria (M. TUBERCULOSIS DES. H37 RA, DIFCO LABORATORIES) was suspended in liquid paraffin (Junsei Chemical Co., Ltd., Japan) at a concentration of 3 mg/mL, and 50 μL was inoculated into the skin at the root of a rat tail. After inoculation, the conditions of the limb ends were evaluated according to the following criteria daily using a scoring system, and the sum of scores for the limb ends was calculated to represent as the arthritis score of the individual.
Score 0: No lesion
Score 1: Flare/swelling is observed in one or more finger joints. Or reddening occurs in the back of the paw with no swelling.
Score 2: Mild swelling occurs in the back of the forelimb or hindlimb.
Score 3: Severe swelling occurs in the back of the forelimb or hindlimb, but not in all fingers.
Score 4: Severe swelling occurs in the back and fingers of the forelimb or hindlimb.

Figure 12A:
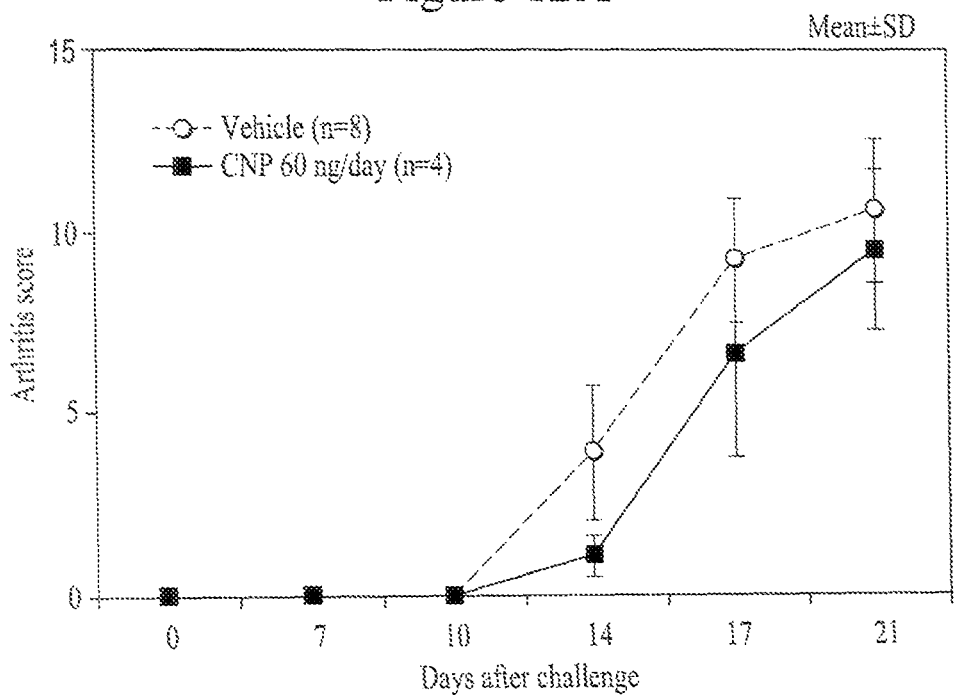
FIG. 12A represents changes in the arthritis score of the limb ends, and it indicates lower arthritis scores for the CNP-22 group.

Results showed that the arthritis score was somewhat lower in the CNP group than in the solvent control group (FIG. 12A).

Figure 12B:
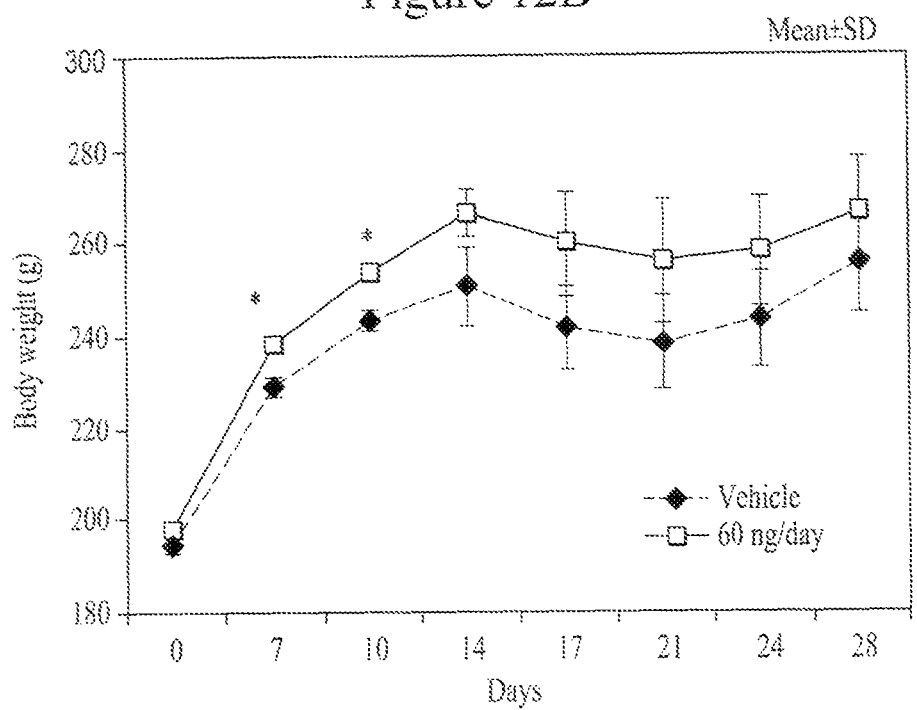
FIG. 12B represents body weight changes, and it indicates that on days 7 and 10 from antigen sensitization, the CNP-22 group showed significantly heavy body weights compared to the solvent control group (vehicle). Unpaired Student's t-test. *: p<0.05 (vs. vehicle).

Changes in body weight were also measured on a daily basis. Results showed that body weight increased significantly in the CNP group compared to the solvent control group (FIG. 12B).

These results revealed that CNPs also inhibit arthritis and improve general condition in an adjuvant rat model.

Example 11

Effect of CNPs on Collagen Arthritis Rat Model

An osmotic pump (2004 model, Durect) containing the solutions below was transplanted subcutaneously in the back of a 10-week-old female DA/Slc strain rat (Japan SLC, Inc., Japan).

Solvent: Distilled water containing 5% dextrose (Junsei Chemical Co., Ltd., Japan), 10% mannose (Nacalai Tesque Inc., Japan) and 5 mmol/L hydrochloric acid (Wako Pure Chemical Industries, Japan).

1 mg/mL solution (6 μg/day) of CNP-22 (Calbiochem Novabiochem).

Immediately after transplantation, bovine type II collagen (Collagen Technology Training Co., Japan) was dissolved in 0.1 mol/L aqueous acetic acid so as to make 1.5 mg/mL and suspended in an equal volume of Freund Incomplete Adjuvant (DIFCO LABORATORIES), and 400 μL of the suspension was inoculated into the skin on the back of a rat. Changes in body weight were also measured on a daily basis. In addition, changes in body weight were also measured in a normal group receiving neither pump transplantation nor inoculation.

Figure 13:
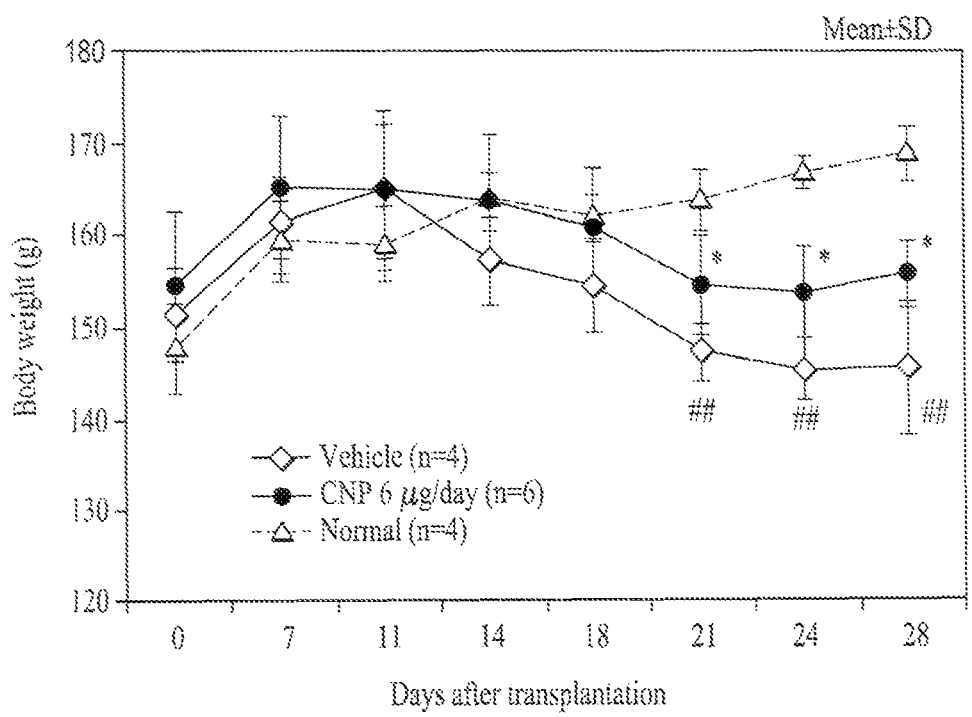
FIG. 13 is a graph showing the effect of CNP-22 on the body weight in a collagen arthritis rat model. It indicates that while on days 21, 24 and 28 from antigen sensitization, the solvent control group (vehicle) showed a significantly light body weight compared to the normal group, the CNP-22 group (CNP 6 µg/day) showed a significantly heavy body weight compared to the solvent control group. Unpaired Student's t-test. ##: p<0.01 (vs. normal), *: p<0.05 (vs. vehicle).

As a result, body weight decreased significantly in the solvent control group compared to the normal group while body weight loss in the CNP group was significantly smaller compared to the solvent control group (FIG. 13). These results revealed that CNPs improve general conditions in a collagen arthritis rat model.

INDUSTRIAL APPLICABILITY

Because the therapeutic or prophylactic agents according to the present invention containing a GC-B activator as an active ingredient can increase the thickness of the articular cartilage and the number of articular chondrocytes, provide resistance to articular swelling, inhibit degenerative changes in articular cartilage, provide markedly decreased changes in synovial cell growth, granulation and inflammatory cellular infiltration, and avoid a decrease in the proteoglycan content in the articular cartilage, they are useful for the treatment or prevention of arthritis including osteoarthritis, such as degenerative gonarthrosis, degenerative coxarthrosis, elbow osteoarthritis, spinal osteoarthritis and temporomandibular arthrosis. Administration of the pharmaceutical composition according to the present invention can result in the inhibition of a reduction in, or the regeneration of, the articular cartilage matrix and chondrocytes in the affected joint portion, and inhibit degenerative changes in articular cartilage and swelling in the articular part, resulting in the inhibition or reduction of arthritic diseases. In particular, because the therapeutic agents for osteoarthritis of the present invention incur less burden and pain on the patient compared to conventional orthopedic operations, such as arthroscopic surgery, artificial joint substitution and osteotomy, they provide superior therapeutic agents with satisfactory QOL for the patient.

The new finding that GC-B activators have the efficacy as described above means that it is possible to inhibit arthritis and promote the growth of articular chondrocyte by activating GC-B. In addition, it is also possible to screen articular chondrocyte growth promoters and therapeutic agents for arthritis by using the GC-B activity (for example, the amount of intracellular cGMP produced) as an indication.

All publications, patents, and patent applications cited herein are incorporated herein by reference in their entirety.

Free Text of Sequence Listing

Description in SEQ ID NO: 1: A disulfide bond is formed between 6-Cys and 22-Cys.

Description in SEQ ID NO: 2: A disulfide bond is formed between 37-Cys and 53-Cys.

Description of artificial sequence in SEQ ID NO: 3: CNP-22 derivative, where a disulfide bond is formed between 6-Cys and 22-Cys.

Description of artificial sequence in SEQ ID NO: 4: CNP-22 derivative, where a disulfide bond is formed between 6-Cys and 22-Cys.

Description of artificial sequence in SEQ ID NO: 5: CNP-22 derivative, where a disulfide bond is formed between 6-Cys and 22-Cys.

Description of artificial sequence in SEQ ID NO: 6: CNP-22 derivative, where a disulfide bond is formed between 1-Cys and 17-Cys.

Description of artificial sequence in SEQ ID NO: 7: CNP-22 derivative, where a disulfide bond is formed between 7-Cys and 23-Cys.

Description of artificial sequence in SEQ ID NO: 8: CNP-22 derivative, where a disulfide bond is formed between 6-Cys and 22-Cys.

Description of artificial sequence in SEQ ID NO: 9: CNP-22 derivative, where a disulfide bond is formed between 1-Cys and 17-Cys.

Description of artificial sequence in SEQ ID NO: 10: CNP-22 derivative, where 4-Xaa=Leu, Ile, Val; 5-Xaa=Lys, Leu, Met; 6-Xaa=Leu, Ile, Ala, Val; 11-Xaa=Ser, Ala, Gly, Thr, Asn; 12-Xaa=Met, Ala, Tip, His, Lys, Ser, Gly; 14-Xaa=Gly, Lys, Ala, Leu; 15-Xaa=Leu, Met and where a disulfide bond is formed between 1-Cys and 17-Cys.

What is claimed is:

1. A method of screening for an articular chondrocyte growth promoter, which method comprises:
   contacting cultured cells, which express guanyl cyclase B (GC-B), with a candidate agent;
   determining the activation of GC-B in the cultured cells,
   selecting the candidate agent which promotes the activation of GC-B;
   contacting the selected candidate agent with articular chondrocytes;
   determining the presence or absence of growth in the articular chondrocytes, and
   identifying the candidate agent as an articular growth promoter if the presence of growth is determined.

2. The method of claim 1, wherein the cultured cells are articular chondrocytes.

3. The method of claim 1, wherein the GC-B activity is determined as an amount of intracellular cyclic guanosine monophosphate (cGMP) produced.

4. The method of claim 1,
   wherein the determining step b) comprises determining an amount of intracellular cGMP produced in the presence and absence of the candidate agent; and
   identifying a candidate agent, which activates GC-B by detecting an increase in the amount of cGMP production in the presence of the candidate agent in comparison to the amount of cGMP production in the absence of the candidate agent.

5. The method according to claim 1, wherein the articular chondrocytes are within an articular cartilage.

6. The method according to claim 5, wherein the presence of growth is determined by measuring an increase in the thickness of the articular cartilage after contact with the candidate agent in comparison to the thickness of the articular cartilage without contact with the candidate agent.

7. The method according to claim 1, wherein the presence of growth is determined by an increase in the number of articular chondrocytes after contact with the candidate agent in comparison to the number of articular chondrocytes without contact with the candidate agent.

8. A method of screening for a therapeutic agent for osteoarthritis, rheumatoid arthritis or other arthritis, which method comprises:
   contacting cultured cells, which express guanyl cyclase B (GC-B), with a candidate agent;
   determining the activation of GC-B in the cultured cells,
   identifying the candidate agent as a therapeutic agent for treating osteoarthritis, rheumatoid arthritis or other arthritis if the candidate agent promotes the activation of GC-B.

9. The method for screening of claim 8, wherein the cultured cells are articular chondrocytes.

10. The method of claim 8, wherein the GC-B activity is determined as an amount of intracellular cyclic guanosine monophosphate (cGMP) produced.

11. The method of claim 8,
    wherein the determining step b) comprises determining an amount of intracellular cGMP produced in the presence and absence of the candidate agent; and
    identifying a candidate agent, which activates GC-B by detecting an increase in the amount of cGMP production in the presence of the candidate agent in comparison to the amount of cGMP production in the absence of the candidate agent.

12. The method according to claim 8, wherein the articular chondrocytes are within an articular cartilage.

13. The method according to claim 12, wherein the presence of growth is determined by measuring an increase in the thickness of the articular cartilage after contact with the candidate agent in comparison to the thickness of the articular cartilage without contact with the candidate agent.

14. The method according to claim 8, wherein the presence of growth is determined by an increase in the number of articular chondrocytes after contact with the candidate agent in comparison to the number of articular chondrocytes without contact with the candidate agent.

* * * * *